(12) United States Patent
Lee et al.

(10) Patent No.: US 7,445,377 B2
(45) Date of Patent: Nov. 4, 2008

(54) NONDESTRUCTIVE RESIDENTIAL INSPECTION METHOD AND APPARATUS

(76) Inventors: Peng Lee, 186 CR 412, Oxford, MS (US) 38655; Kevin J Seddon, 101 Cedar Hill Rd., Oxford, MS (US) 38655

( * ) Notice: Subject to any disclaimer, the term of this patent is extended or adjusted under 35 U.S.C. 154(b) by 151 days.

(21) Appl. No.: 10/708,571

(22) Filed: Mar. 11, 2004

(65) Prior Publication Data

US 2004/0190586 A1    Sep. 30, 2004

Related U.S. Application Data

(60) Provisional application No. 60/453,856, filed on Mar. 12, 2003.

(51) Int. Cl.
  *G01N 25/72* (2006.01)
  *G01J 5/00* (2006.01)
(52) U.S. Cl. .............. 374/5; 374/121; 374/57; 374/123
(58) Field of Classification Search ........ 374/121, 374/4, 5, 45, 57, 124, 137
  See application file for complete search history.

(56) References Cited

U.S. PATENT DOCUMENTS

| | | | |
|---|---|---|---|
| 3,791,097 A | 2/1974 | Cassella et al. ............ 52/741 |
| 4,396,137 A | 8/1983 | Benjamin ................ 224/257 |
| 4,550,376 A | 10/1985 | Maciejczak ............... 364/512 |
| 4,647,220 A | 3/1987 | Adams et al. .............. 374/5 |
| 4,768,158 A | 8/1988 | Osanai ................... 364/507 |
| 5,444,241 A | 8/1995 | Del Grande et al. ........ 250/253 |
| 5,631,465 A | 5/1997 | Shepard ................... 250/330 |
| 5,637,871 A | 6/1997 | Piety et al. ............... 250/330 |
| 5,719,395 A | 2/1998 | Lesniak .................. 250/330 |
| 5,742,335 A | 4/1998 | Cannon ................... 348/135 |
| 5,834,661 A | 11/1998 | Nonaka et al. ............. 73/866 |
| 6,028,625 A | 2/2000 | Cannon ................... 348/135 |
| 6,192,325 B1 | 2/2001 | Piety et al. ............... 702/184 |
| 6,516,084 B2 | 2/2003 | Shepard ................... 382/141 |
| 6,647,091 B2 | 11/2003 | Fenkart et al. ............. 378/57 |
| 6,714,017 B2 | 3/2004 | Enacheseu et al. .......... 324/501 |
| 6,751,342 B2 | 6/2004 | Shepard ................... 382/141 |
| 2001/0001851 A1 | 5/2001 | Piety et al. ............... 702/184 |
| 2003/0230717 A1 | 12/2003 | Reilly et al. .............. 250/341.6 |
| 2004/0162710 A1 | 8/2004 | Schwartz .................. 703/2 |

OTHER PUBLICATIONS

Argentino, "100's of Tips on Saving Energy and Money at Home" (www.mississauga4sale.com/newsletter/energy_saving_tips.htm), Jul. 16, 1996.*

(Continued)

*Primary Examiner*—Edward Lefkowitz
*Assistant Examiner*—Mirellys Jagan
(74) *Attorney, Agent, or Firm*—Baker Donelson Bearman Caldwell & Berkowitz PC

(57) ABSTRACT

This invention provides an apparatus for nondestructive residential inspection and various methods for using a thermal imaging apparatus coupled to inspect exterior residential components, interior residential components, a pitched roof and basement of a residential building and the electrical system of a residential building.

7 Claims, 24 Drawing Sheets

OTHER PUBLICATIONS

"Checklist for Energy Efficiency in Buildings", www.arch.hku.hk/~cmhui/teach/SBT/check.pdf, Oct. 9, 1999.*

"ASHI Standards of Practice", American Society of Home Inspectors, http://www.inspect-ny.com/ashi/standards00.htm, Jul. 8, 1999.*

"Infrared Energy Audit", Predictive Maintenance Co., www.predictive-maintenance.com/energy.html, Jun. 27, 2001.*

"Home Energy Audit", www.montgomerycountymd.gov/mc/services/dep/Energy/audit.htm, Jan. 12, 1999.*

"Thermal insulation—Qualitative Detection of Thermal Irregularities in Building Envelopes—Infrared Method" International Standard ISO 6781 1983.

"Standard Practice for Thermographic Inspection of Insulation Installations in Envelope Cavities of Frame Building" ASTM International 2003.

"ThermalScan IRC-2000 Infrared Camera" InspectorTools.

"Infrared Imaging for Home Inspections" Monroe Infrared Technology.

"Monroe Infrared Technology" Monroe Infrared Technology 1984.

"K6800 Spectra Scan" Monroe Infrared Technology.

"Standard Practice for Location of Wet Insulation in Roofing Systems Using Infrared Imaging" ASTM International.

"Infrared Inspection" Boldstar Infrared Services Feb. 28, 2001.

Mark Gilbert, Thermal Imaging Puts Termites in the Red, National Center for Preservation Technology and Training, Nov. 2001.

Jan Suskin, Taking Aim at Formosan Subterranean Termites, Agricultural Research, Oct. 2000, vol. 48, No. 10, pp. 12-15.

David Rice, General Thermography, Snell Infrared Message Boards, Nov. 8, 2000.

Amy Spillman, Operation Full Stop: Stopping the Swarm, Agricultural Research, Jul. 2003-vol. 51 No. 7, p. 4-8.

USDA Agricultural Research Service, 2004 Annual Report.

John Snell, Thermographic Applications, Snell Infrared Message Boards, Jul. 22, 2002, U.S.A.

National Park Service, FY 2004 Budget Justifications, Activity: Cultural Programs, p. NR & P-30-44, FY 2002 p. 37.

Jon L. Grossman, IR Thermography as a Tool for the Pest Management Professional, IR Info, 2004, Proceedings Paper.

Ken James, Finding Termites with Thermal Imaging, Infra Mation 2002, Sep. 29-Oct. 2, 2002, Orlando, Florida.

Bill Draft, Re: Locate Hidden Termite Damage, Snell Infrared Message Boards, Dec. 27, 1997.

Thermal Inspection Services "Residential Inspections" "New Home Inspections".

Infrared Training Center "infrared Building Science".

Infrared Thermography "SBA Thermographics" Jul. 21, 2001.

Maverick "Infrared Thermography: Indoor Electrical Applications".

Maverick "Infrared Thermography: Building Applications".

* cited by examiner

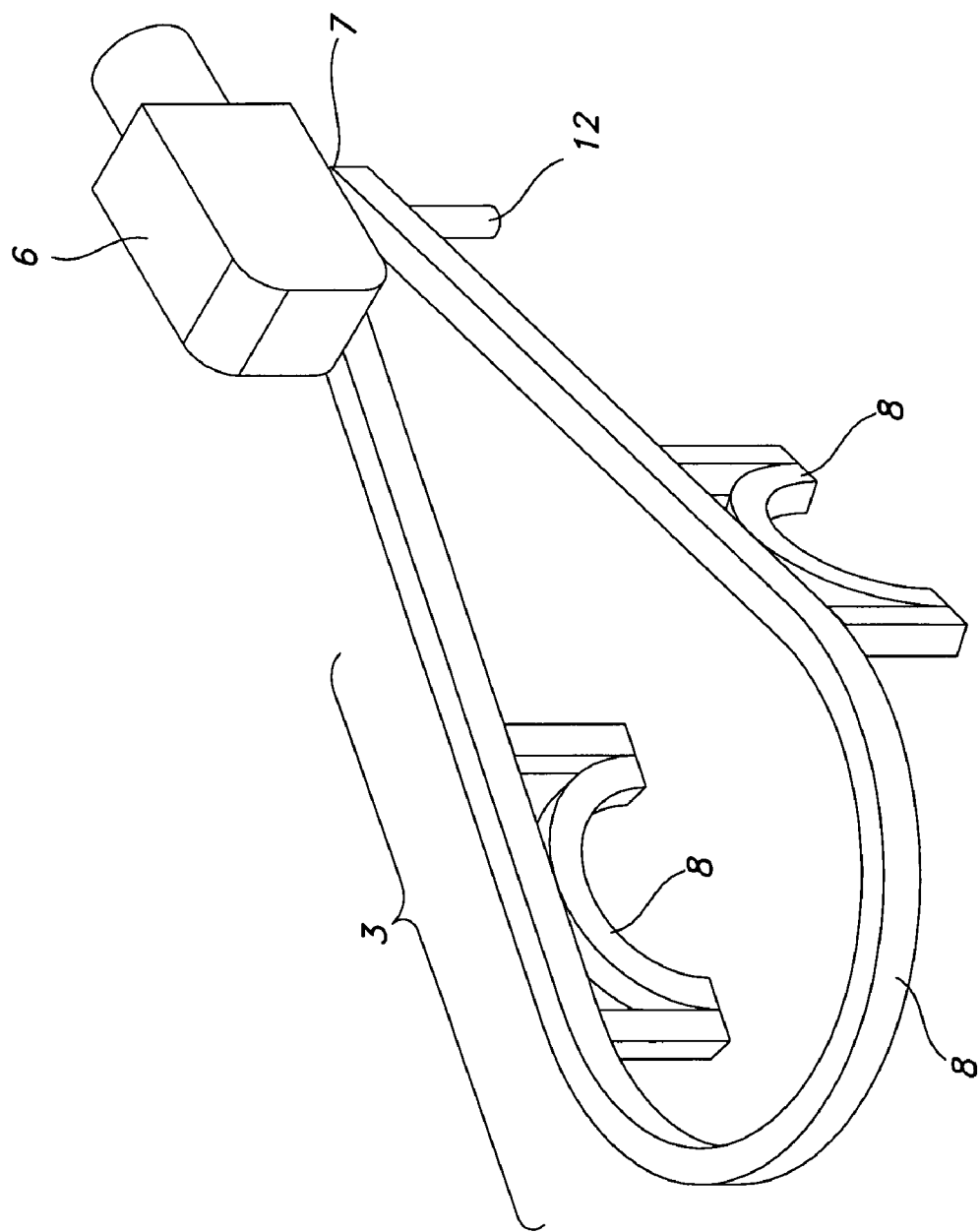

48

49

NONDESTRUCTIVE RESIDENTIAL INSPECTION METHOD AND APPARATUS

CROSS REFERENCE TO RELATED APPLICATIONS

This Application claims the benefit of U.S. Provisional Application No. 60/453,856 filed Mar. 12, 2003 under 35 U.S.C. Section 119(e) (hereby specifically incorporated by reference in its entirety)

BACKGROUND OF INVENTION

This invention relates to the field of nondestructive residential inspection.

Infrared thermography (thermal imaging scan) has been used in industrial electrical, mechanical, and boiler evaluations. In these applications, true temperature measurements are made of the structure being evaluated. True temperature evaluations require expensive equipment and time to take temperature measurements. Additionally, infrared imaging is used for (ASTM standard #C-1153) locating wet insulation in flat roof system. Most commercial, industrial, and institutional roofs are flat roofs. However, there is no guideline or standard for pitched roofs inspection using thermal imaging. Infrared thermography has also been used to provide "energy audits" of homes (ISO 6781 and ASTM C 1090-90) and industrial electrical panel inspections. More specific, diagnostic applications of infrared technology for residential applications, however, require greater contrast between building components shown in the scanned images.

SUMMARY OF INVENTION

This invention provides a method to conduct a complete inspection of a residential building. A complete inspection includes the steps of: conducting an infrared scan of a residential building, conducting a visual home inspection and conducting an acoustic scan to detect wood destroying insects. The term infrared scan of a residential building includes all of the methods discussed infra in the section on infrared scanning methods.

This invention further relates to the following methods and devices for inspecting residential buildings. This method includes a thermal imaging (infrared) camera for looking into, examining and evaluating a building's structural and systemic components, such as walls, insulation, electrical wiring, heating, air conditioning and plumbing. This method captures temperature profiles, which provide valuable information to evaluate and/or further investigate problems in the building. Additionally, this method includes procedures for creating favorable conditions for a thermal imaging scan to detect concealed and/or nonconcealed conditions of the building's components.

More specifically, this invention relates to a method to rapidly inspect residential building components for a designated entity such as a home owner, a realtor, an insurance company or any designated party. This method involves creating a temperature differential of greater than 10° F. between the inside and the outside of the residential building. It also involves turning on substantially all light switches and substantially all exhaust blowers in the residential building and obtaining temperature profiles of the exterior residential building components selected from the group consisting of wall, eave and facia. It also involves obtaining temperature profiles of the interior surface of a pitched roof; obtaining temperature profiles of the interior residential building components; and obtaining temperature profiles of each electrical circuit in a residential building. Additionally, this invention relates to creating sufficient air flow in a basement to facilitate evaporation; and obtaining temperature profiles of a basement wall and assessing each of the temperature profiles to detect a thermal anomaly indicative of a problem with the residential building components; and reporting a problem to the designated entity.

It is a first objective of the invention to provide a nondestructive yet reliable method and apparatus for more accurate assessment of the condition of a residential building's components very quickly and to provide good record-keeping in regard to the building's condition.

It is a second objective of the invention to provide a procedure that creates a significant variation in temperature among the building's components in relation to the temperature outside the building. This process is carried out by introducing cold or heated air to the building, either through the building's own heating or cooling system or through external injection of cold or hot air to the building's interior.

These objectives are achieved, in accordance with the principles of a first preferred embodiment of the invention, by providing a method and apparatus for monitoring and recording the temperature profiles of a building's components and structure.

Traditional home inspection primarily involves human visual inspection of a building's components. Since the human eye cannot see through walls and other solid objects, traditional visual inspection is limited to the surface level. Our preferred embodiment employs a thermal imaging sensor (infrared camera) that allows the inspector to view and inspect beyond the surface level through evaluation of the temperature profiles of building components due to the difference in thermal properties between building components.

The overall goal of the thermal imaging (infrared) home inspection system is to detect problems in buildings accurately and as early as possible. Early and accurate detection of a building's problems reduces further damage and provides valuable, more accurate and realistic information to all concerned parties, such as the building owner, the building seller, the real estate company, the loan company, the insurance company and, most important, the buyer.

Infrared detection has the advantage of covering a large area. It provides efficient screening and a convenient way of scanning the structure for potential problems in order to alert the inspector to carry out a more specific inspection.

In accordance with another aspect of the preferred embodiment of the invention, the infrared scan is combined with a procedure to create a temperature differentiation between indoor and outdoor areas. This procedure provides the infrared camera with favorable conditions for scanning.

Because different seasons of the year generate different weather conditions, a building experiences large fluctuations of temperature, humidity and atmospheric pressure changes. At certain times of the year, such as spring and fall, the outdoor temperature can be very close or equal to the indoor temperature. This reduction of the difference between indoor and outdoor temperatures greatly reduces the thermal imaging (infrared) device's ability to "see" inside the building's components.

The preferred procedure of the invention creates a larger temperature contrast between the building's components, thus greatly increasing the effectiveness of the thermal imaging system. The bigger the temperature contrasts between the building's components, the better the temperature profiles will be.

In the other preferred embodiment these images of temperature variations can be recorded with a digital or analog image-recording device such as a camcorder.

Finally, according to yet another aspect of the preferred embodiment of the invention, recorded temperature profiles taken at each inspection site using the above-summarized methods and apparatus may be provided to a central operations unit for use in building a central database of information. The central operations unit may operate on a nationwide or even worldwide basis and serve as a facility of data communications, data acquisition, data analysis, continuous updating of temperature profiles, references and aggregation of inspection results. The accumulated data may be made available to entities interested in the building's condition, thereby providing an invaluable resource of building information. No such centralized resource is currently available.

BRIEF DESCRIPTION OF DRAWINGS

FIG. 3 is a schematic illustration of an alternate embodiment of the apparatus.

DETAILED DESCRIPTION

Figure 1:
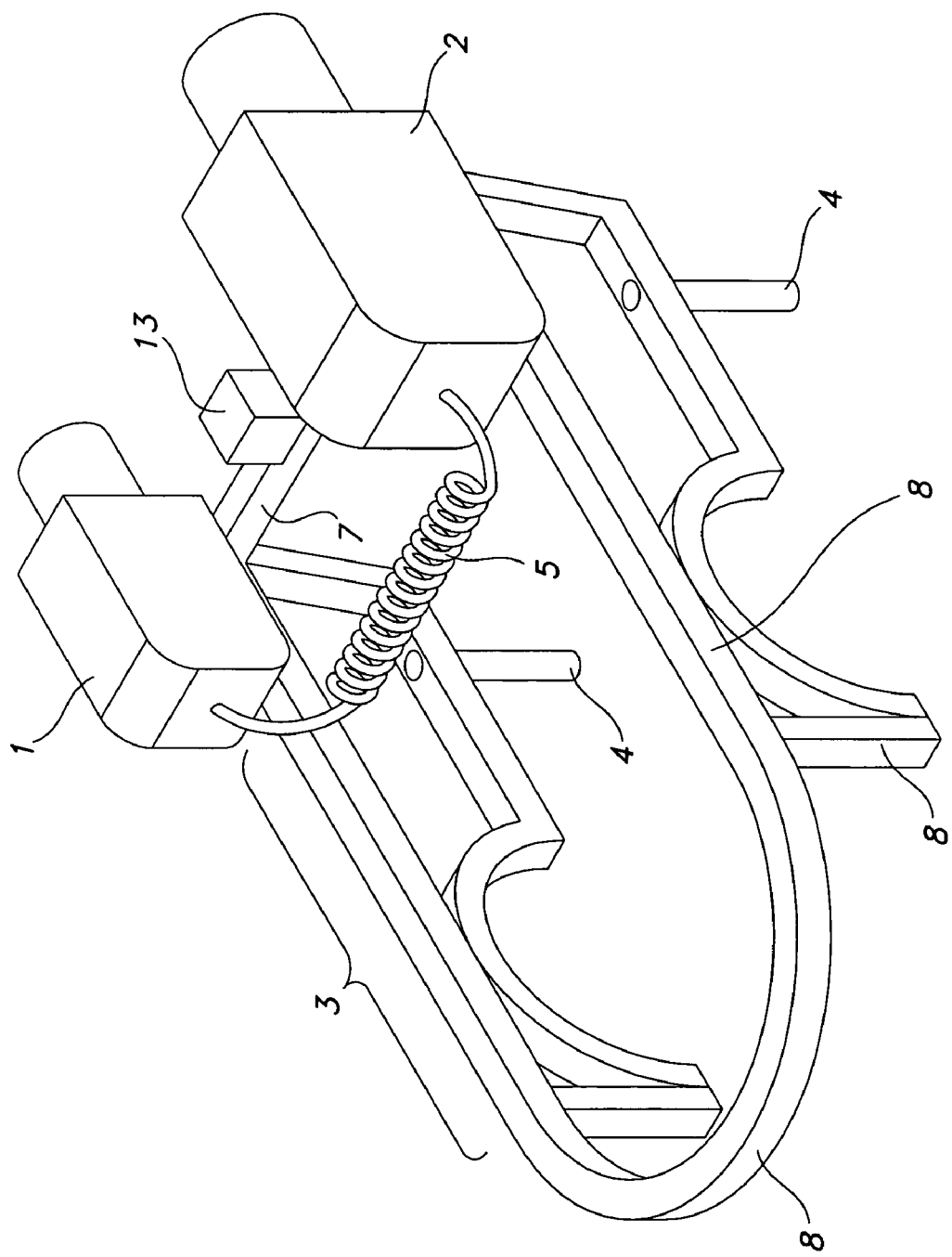
FIG. 1 is a schematic illustration of a nondestructive thermal imaging apparatus in accordance with the principles of a preferred embodiment of the invention.

A home inspection is a thorough visual examination of a home's structural and systemic condition. A home inspection evaluates the physical condition of the home, identifies items that may need repair or replacement and identifies systems and components that are nearing the end of their service life.

Because a home purchase is one of the biggest investments a person will ever make, a home inspection is crucial in providing valuable information about the investment. It also assists in protecting against unknown and costly repairs that may not be obvious to the untrained eye. Items covered typically include the property's wall, roof, structural components and major electrical, plumbing and operating systems.

Major areas of investigation in a home inspection include: I. Improper electrical wiring, such as open ground, hot and neutral reverse, inadequate overload protection, and hazardous wiring connections; II. Roof damage and leakage caused by old or damaged shingles and improper flashing; III. Poor overall maintenance as evidenced by such signs as cracked; makeshift wiring or plumbing; broken fixtures; IV. Structural issues, including damage to such structural components as foundation walls, floor joists, rafters and window and door headers; V. Improper surface grading and drainage problems, such as water penetration into the basement area or crawl spaces; VI. Flaws in the home's exterior, including doors, windows, door and wall surfaces, which may result in air or water penetration. Inadequate caulking or weather stripping are common culprits; VII. Ventilation problems which may result in excessive interior moisture, rotting and premature failure of both structural and nonstructural elements; and VIII. Depending on location, miscellaneous concerns such as the presence of mold, wood-destroying insects, able to see signs of rodents in the ceiling.

A home inspection to be of value to a home owner needs to be complete; however, a residential inspection to be affordable must be completed within a reasonable period of time. This invention provides a method to conduct a complete inspection of a residential building within a cost effective period of time, i.e., two hours for a residential building of 2,000 sq. ft. or less, and four hours for a residential building between 3,000 to 4,000 sq. ft. The complete inspection includes several parts. One part is an infrared scan of the residential building. This type of inspection is discussed in detail, infra. Another part of a complete or "traditional" inspection is a visual inspection. A visual inspection is defined by ASHI, NAHI, and NABIE protocols. Another part of the inspection is an acoustic scan of the residential building for wood destroying insects such as termites. The procedures to conduct termite acoustic detection are set out in U.S. Ser. No. 10/680,377 filed Oct. 7, 2003 (hereby specifically incorporated by reference in its entirety—specifically, the software program at pages 28 through 42 which facilitates the acoustic detection of wood destroying insects). A report can be generated which summarizes all portions of the inspection.

Infrared Scanning Methods and Apparatus—Infrared scanning works because different parts of a building's components retain different temperatures due to the individual component type's thermal properties, such as heat capacity, heat transmission, heat retention and heat dissipation. The difference between indoor and outdoor temperatures creates a temperature gradient, causing the heat to transmit from high temperature areas to low temperature areas. Due to the different thermal properties of different residential building components, heat transmits and dissipates through these different residential building components at different rates.

Take a building's wall in the summertime, for example: When scanning the interior wall with an infrared camera, fiber grain insulation transmits much less heat than a 2×4 stud; the 2×4 stud thus has a higher temperature which can be easily registered by the infrared sensor (camera). Infrared detection also has the advantage of covering a larger area very quickly and provides the inspector with critical information about potential problem areas in order to guide the inspector to carry out more specific tests and inspections.

Because different seasons of the year generate different weather conditions, a building experiences large fluctuations of temperature, humidity and atmospheric pressure changes. At certain times of the year, such as spring and fall, the outdoor temperature can be very close or equal to the indoor temperature. This reduction of the difference between indoor and outdoor temperatures greatly reduces the thermal imaging (infrared) device's ability to "see" inside the building's components.

The preferred procedure of the invention creates a larger temperature contrast between the building's components, thus greatly increasing the effectiveness of the thermal imaging system. The bigger the temperature contrasts between the building's components, the better the temperature profiles will be. The procedure involves activating the building's own heating or cooling system for a certain period of time prior to the inspection. The duration can be as brief as one minute to as lengthy as a few hours, depending on the size (capacity) of the heating/cooling system and the size and condition of the building. At a certain point of the heating or cooling process, the temperature contrast reaches a workable condition for the thermal imaging sensor. Therefore, the inspector will have to periodically check the conditions with the thermal imaging camera. The decision to activate either the heating or cooling mode of the building's heating/cooling system will depend on the outdoor temperature. A preferred rule of thumb is to let the inspector make this judgment: If he feels it's cold outside (below 70° F.), he will activate the heating system; if he feels that it's hot outside (above 70° F.), he will activate the cooling system. In the event that the building is not equipped with a heating or cooling system, an external heating or cooling unit can be employed to achieve a similar effect. In this method, a temperature differential of greater than 10° F. between the inside and the outside of the building is created. This can be achieved by running either the heating or air conditioning system until the desired temperature differential is obtained.

As schematically illustrated in FIG. 1, the preferred embodiment of the invention includes a thermal imaging (infrared) camera 1 for performing a scan of residential building components in order to locate potential problems in the building. An infrared camera is an apparatus that converts the spatial variations in infrared radiance from a surface into a two-dimensional image, in which variations in radiance are displayed as a range of colors or tones. In this application, it is preferred that the image is displayed as tones, with dark shades representing cold and light shades representing hot infrared radiance. This is commonly called the gray scale. Gray scale work is best for home inspection because it is less confusing; however, color is also sufficient for home inspection.

The temperature profiles created by the thermal imaging camera can be assessed to detect a thermal anomaly indicative of a problem with the residential building components. In the preferred embodiment, each of the temperature profiles is assessed for an anomaly; however, in certain situations where time is limited or a specific problem is being addressed, at least one of the thermal anomalies are assessed for a problem.

A problem in a residential building component will appear as an anomaly in a temperature profile. An anomaly is any deviation from the normal characteristics of a specific type of residential building component. FIGS 4, 13A-E and 15-31 show a series of temperature profiles and temperature profile anomalies. A temperature profile anomaly is indicative of a possible problem with the residential building component. These building problems include but are not limited to the following: structure, insulation, moisture, electrical hot spots, water leakage, unwanted pests such as termite, mice, and rats, and air duct leakage. The term residential building components include elements of a building, such as walls, ceilings, windows, plumbing fixtures, etc. The residential building component can be an exterior component, such as exterior wall (wood, bricks, stucco, EIFS or vinyl siding), eaves, fascias and interior surface of a pitched roof. Similarly, the residential building component can be the electrical system. Additionally, the residential building component can be an interior structure, such as insulation, wiring, air duct, and finished surfaces.

The corresponding video images of the potential building problems are recorded by digital video camera 2. A digital video camera 2 is a means to record a digital image. The thermal imaging camera 1 is connected to digital video camera 2 by cable 5. The video output of the infrared camera 1 is input to the video recording device. Thermal imaging camera 1 may be any of a number of commercially available infrared cameras conventionally used by structural engineers, police and the military. In order to improve the accuracy by which thermal imaging camera 1 detects potential problems, the thermal imaging camera 1 may further include target recognition software, such as matched filtering software which compares the frequency spectra of reference images, thereby reducing the level of skill required of the camera operator.

While the invention is not limited to a particular thermal imaging (infrared) camera 1, there are various thermal imaging systems that are sensitive enough and capable of evaluating residential building components. For example, Raytheon's Control IR2000B or 300D thermal imaging system, although not the most sensitive, has shown good consistency and accuracy. It is robust and, most importantly, relatively inexpensive. Those skilled in the art will appreciate that it is also possible to use other types of thermal imaging cameras 1 so long as they are sufficiently sensitive to detect temperature variations normally down to 0.12 degrees Celsius or lower (e.g., 0.08 degrees Celsius) and cover an approximate frequency range of the infrared spectrum emitted by residential building components. The infrared detector resolution is preferably 240×320 or higher; but can be 120×160 (with a good thermal window). It will, of course, be appreciated by those skilled in home inspection that the thermal imaging camera 1 and the digital video camera 2 may be combined into a combination unit 6 as shown in FIG. 3. However, a combination unit 6 presently carries a much higher price tag, which makes the residential application much less attractive.

Figure 2:
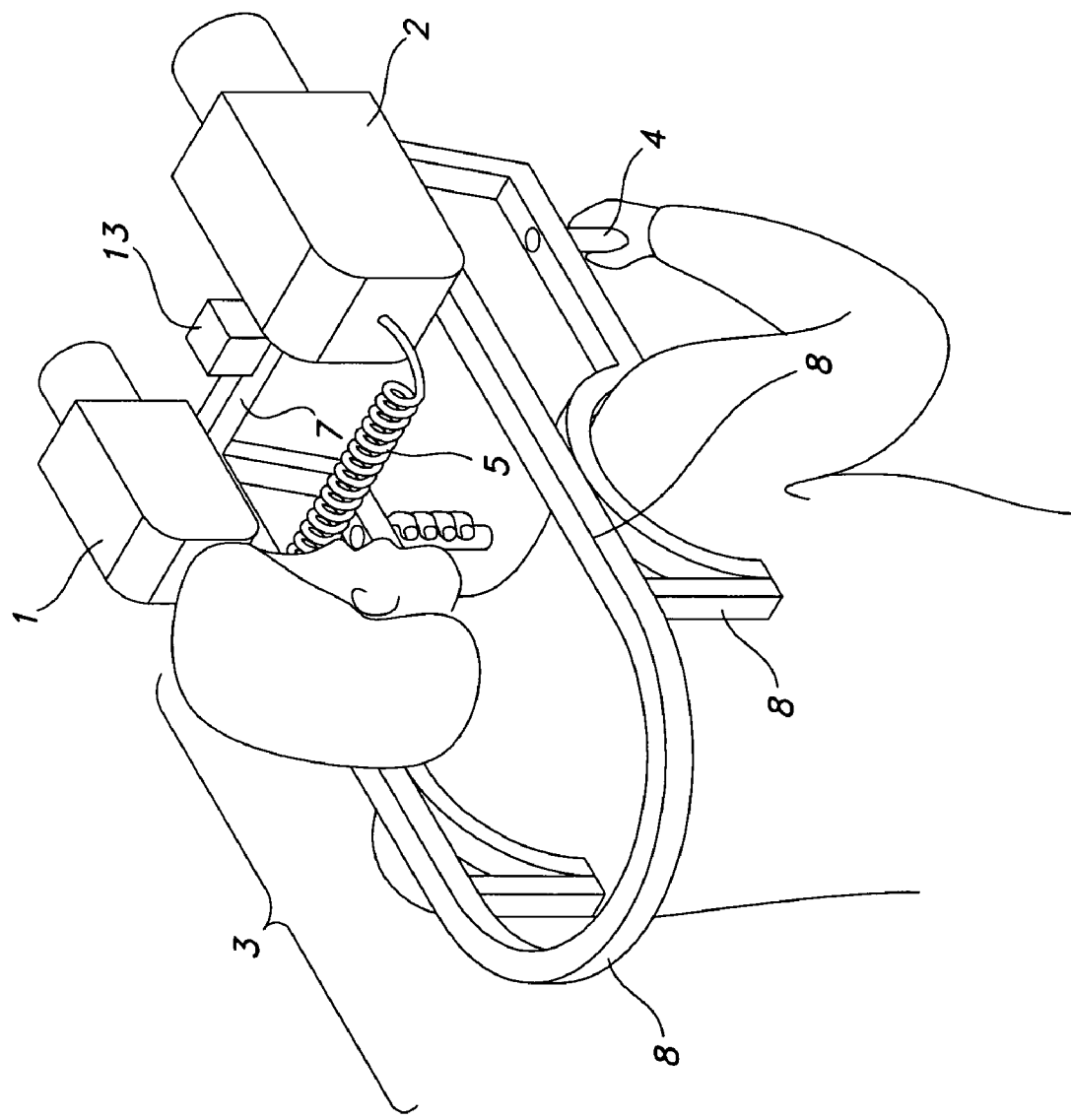
FIG. 2 is a schematic illustration of a nondestructive thermal imaging apparatus in accordance with the principles of a preferred embodiment of the invention.

While one particularly preferred embodiment is the new arrangement specifically designed to securely position the device in front of the inspector for ease of operation, out of harm's way to protect the sensitive infrared camera, and to allow the inspector to have both hands free when needed to move an object. As shown in FIG. 1, a harness apparatus 3 allows both the thermal imaging camera 1 and the digital video camera 2 to be mounted in a balanced, safe and easy-to-use position for the inspector. As shown in FIG. 2, the harness apparatus 3 is designed to be securely mounted over the inspector's shoulders. The harness apparatus 3 allows the operator to operate with his hands with the aid of the handles 4 or without hands in the event that the hands need to be free to perform other functions, with add chest support (not shown) The harness apparatus 3 is configured to support at least one residential inspection device. The residential inspection device can include, for example, a thermal imaging camera, a thermal imaging camera, video recording device, a means to transmit or record a digital video image, such as a LCD or a digital camera, a combination unit thermal imaging camera recording and a wireless communication apparatus.

More specifically, the harness apparatus 3 in the preferred embodiment has a first portion 7 for supporting at least part of a thermal imaging camera 1 and if desired at least part of the video recording device 2 such as a digital video camera. In this embodiment, the thermal imaging camera 1 and the video recording device 2 are attached to the first portion 7 of the harness 3. This first portion 7 is connected to a second portion 8. The first and second portions form an enclosure. The enclosure is of sufficient size to accommodate a human torso as shown in FIG. 2. The thermal imaging camera 1 in this embodiment is operably connected via a cable 5 to a video recording device 2.

The second portion 2 is generally "U shaped" with the leg portions of the "U" being sufficiently spaced apart to accommodate a human torso. The second portion 8 can function to support at least part of the thermal imaging camera 1 and at least part of the digital video camera 2. The second portion 8 is configured to receive the shoulder portions of a human. The term configured to receive the shoulder portion of the human torso means that the second portion 8 rests on the shoulder so that the harness 3 is above the shoulders. In one embodiment, the residential inspection devices are attached to the second portion. The first portion 7 and second portion 8 are configured to support at least one residential inspection device in that they provide a flat, rigid platform for the residential inspection devices. The second portion 8 can include a plurality of handles 4 which project generally downwardly. The plurality of handles 4 may be of any shape to be gripped by the hand of the person wearing the harness apparatus 3. The second portion 8 can be formed of two parts to make a more rectangular enclosure (not shown).

In the alternate embodiment shown in FIG. 3, the harness apparatus 3 is a generally triangular shaped substantially one piece unit. In this embodiment, a combination unit thermal imaging camera recording device 6 is affixed to the first portion 7 of the harness apparatus 3. The harness apparatus 3 includes a portion 8 adopted to retain the shoulder portion of a human torso. A single handle 12 can be made one piece with the unit or attached to the harness apparatus 3.

The embodiment shown in FIGS. 1 and 2 can include a means to transmit a digital image to a central receiving facility. This communication apparatus 13 can be affixed to harness apparatus 3. Various wireless communication apparatus are known to those skilled in the art, such as a wireless internet communication system.

Exterior Residential Application—The use of the infrared equipment for exterior inspection has proved beneficial in cases where the exterior clad is made of wood and wood product siding, EIFS, or vinyl siding. The thermal properties of these materials are such that the infrared camera can discern moisture infiltration, some structural anomalies, and the occasional insect infestation. The same can be said for inspection of eaves and fascias utilizing the infrared equipment.

There are some cautions that the user has to be aware of, however. First and foremost, if the infrared equipment is being used outdoors, the current weather conditions should be an obvious consideration. Precipitation of any kind will damage the electronics, the digital camera and the infrared camera.

Another consideration is the position of the sun. The thermal load provided by direct, or indirect, sunlight (also called solar load) is tremendous and cannot be compensated for by the equipment. Therefore, successful use of the infrared sensor depends on the time of day and solar position. The user may have to delay or reschedule use of the infrared equipment on a particular part of the house that is currently in full sun. Solar loading can, however, provide opportunities for infrared investigations of exteriors that ordinarily would not be possible. Successful use of the equipment on exterior surfaces depends on access to a thermal window. The thermal window represents the optimum opportunity for the infrared camera to discern thermal differences within building components. The optimal time to catch the thermal window for exterior wall surfaces are after sunset and after sunrise.

More specifically, conditions for obtaining a good thermal window are: sunny day, little to no wind, and clear sky. During the summer time, a thermal window begins to open around an hour to a couple of hours after sunset and after sunrise when sun energy begins to heat up the wall surfaces. In the wintertime a thermal window may begin to open as early as a few minutes after sunset and right after sunrise, depending on where you are. The colder the location is, the faster the thermal window will open.

Thermal capacity is the physical property of a material's ability to store energy. The materials in a wall assembly have relatively low thermal capacitances when compared to water. Water requires a lot of energy to raise its temperature and likewise must release a lot of energy to cool down. Therefore, moisture in a finished exterior wall will appear as cold spot during the after sunrise thermal window period on the other hand it will appear as warm spot during the after sunset thermal window. This phenomenal provides us a very useful way of inspecting moisture within finished exterior wall such as various type of siding (steel, vinyl, etc.), stucco, Exterior Insulation Finish System(EIFS). However, it should be noted that a thermal window exists when there is a differential temperature between building components. This can occur if one of the components includes moisture or if one of the components is being differentially heated by the sun.

Thermal window for inspecting within either finished exterior wall, interior wall or exterior roof overhang (eaves) can also be obtained when moisture allowed to evaporate. In order for water molecule to evaporate it must absorb heat energy from its surrounding as a result the moisture spot appear as cold spot. When the thermal window opens, the operator will be able to see more and more visual definition of the thermal differences within building components and its components. This means that as the window opens, the internal components of a wall's structure will become more and more pronounced as displayed on the video screen of the equipment, leading to better resolution and increased accuracy of the inspection.

Figure 4A:
FIG. 4A is a visual photograph of an EIFS wall.
Figure 4B:
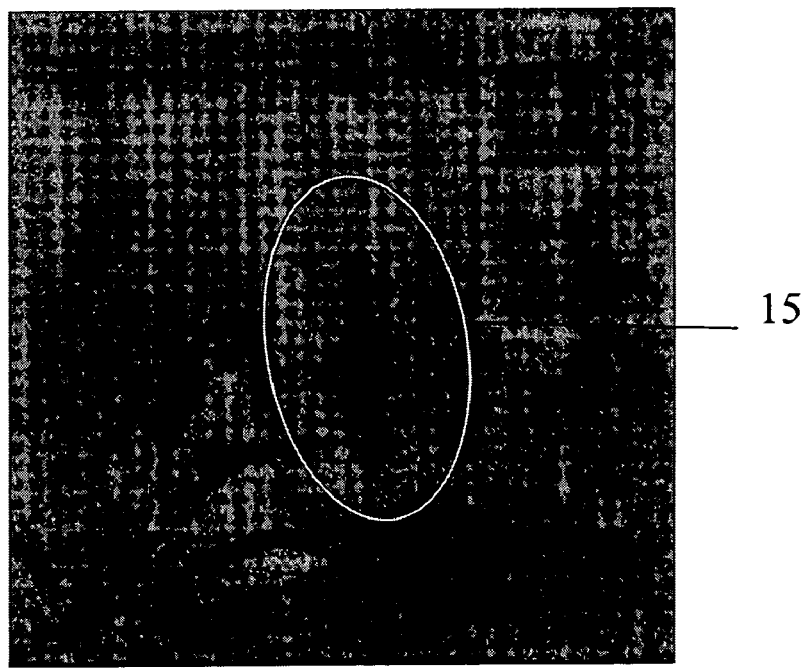
FIG. 4B is a temperature profile of an EIFS wall.

More specifically, this process relates to an inspection of an exterior residential building component. The exterior residential building component is selected from the group consisting of: wall, fascia, and eave. The process of obtaining a temperature profile of an outside residential component implies that a thermal window exists, in that, a useful temperature profile could not be obtained without thermal differences between components. The next step involves obtaining a temperature profile of the exterior residential building components. Then, a temperature profile is recorded on a digital recording device. The digital recording is reviewed to detect any thermal anomalies. Now referring to FIG. 4A, an EFIS exterior wall is shown with a regular video photograph. In FIG. 4B, a temperature profile, taken in the morning after sunrise when the thermal window has just begun to open shows a warm spot 15 which in indicative of moisture within an EFIS wall.

Figure 5A:
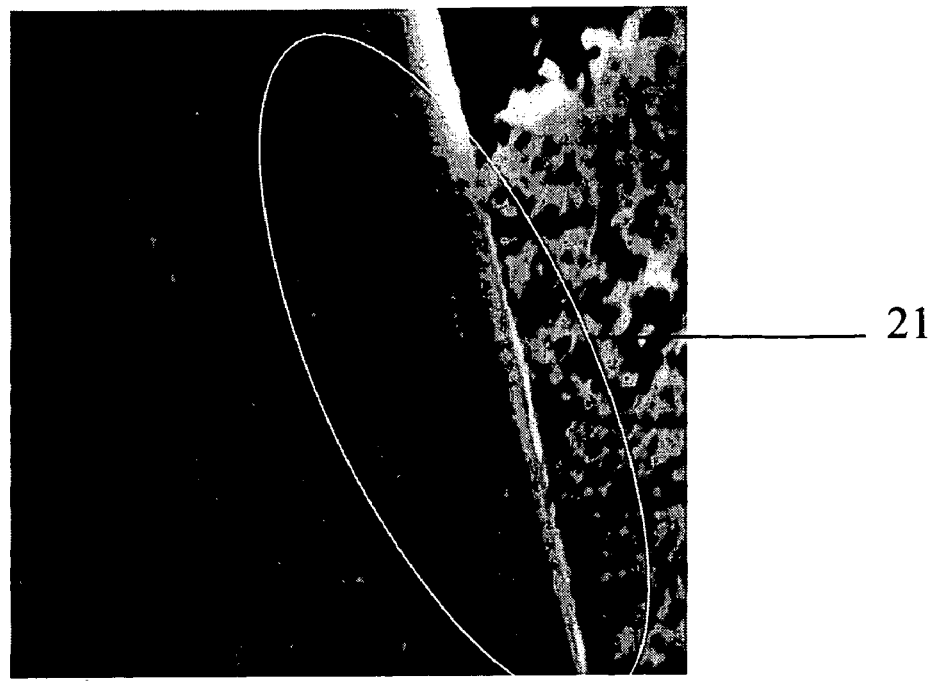
FIG. 5A is a temperature profile of vinyl siding.
Figure 5B:
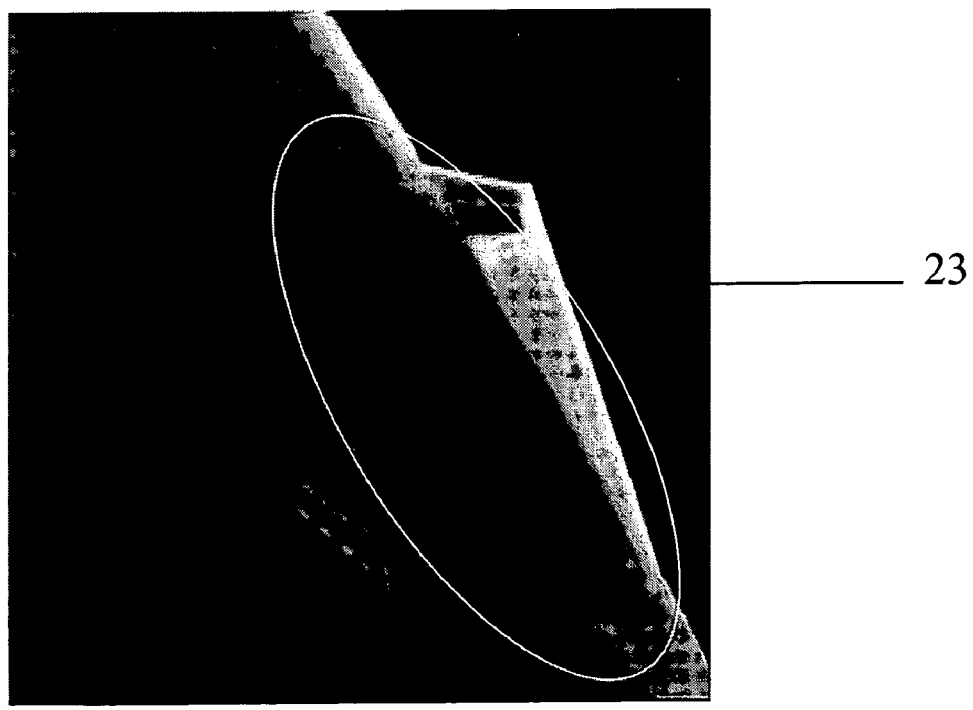
FIG. 5B is a temperature profile of vinyl siding.

In FIGS. 5A, and 5B, temperature profiles, taken when moisture is allowed to evaporate shows anomalies as dark spots 21 and 23 under the vinyl siding. This moisture is not visible to the human eye. These anomalies 21 and 23 are indicative of the presence of moisture under the vinyl siding.

Figure 6:
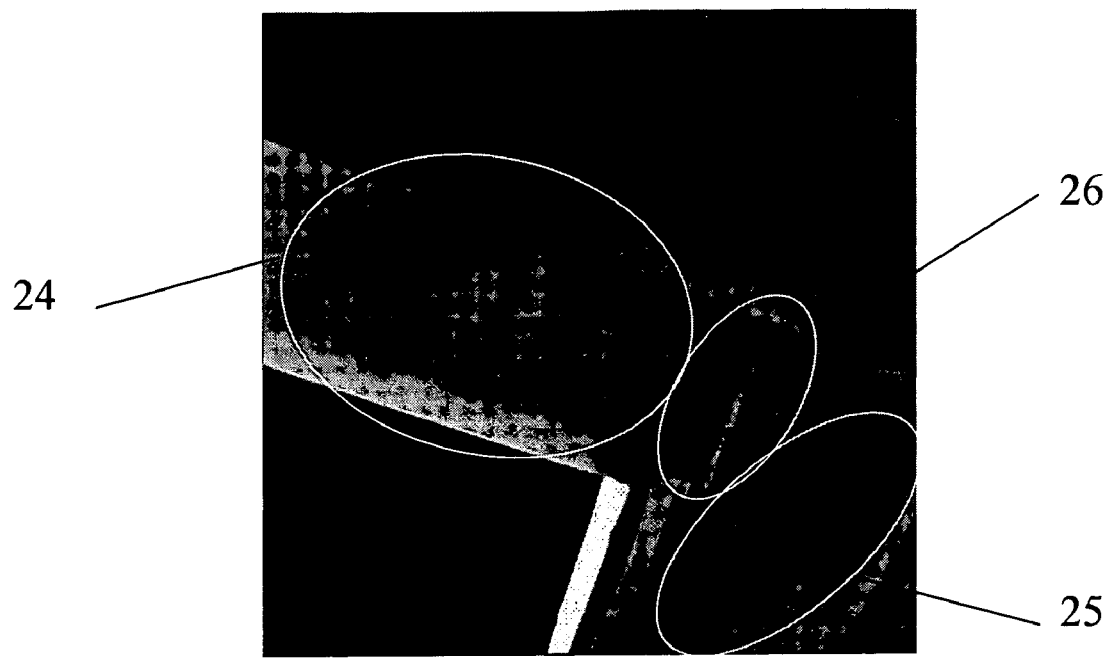
FIG. 6 is a temperature profile of an eave.

Now referring to FIG. 6, a temperature profile, taken in the morning after sunrise of an eave shows a number of anomalies. Anomaly 24 and 25 are indicative of current structural deformations due to past infiltration of water (dried) and anomaly 26 is indicative of the presence of moisture.

Figure 7:
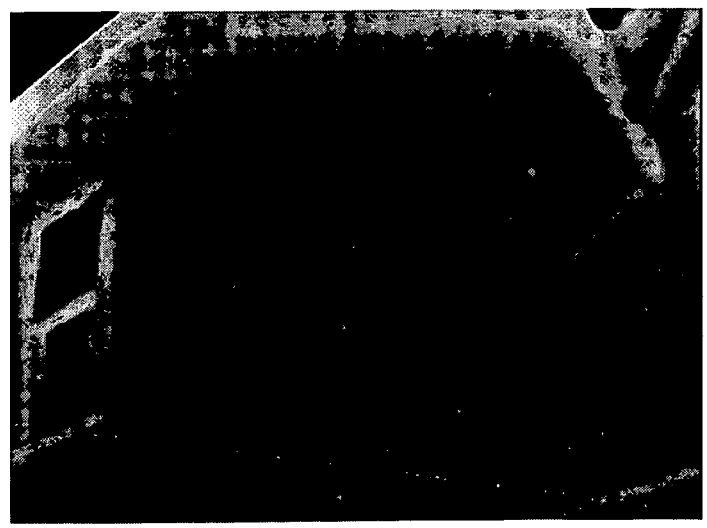
FIG. 7 is a temperature profile of an EIFS wall.

FIG. 7 shows a temperature profile taken in the morning of a dry EIFS wall showing no thermal anomalies.

Figure 8:
FIG. 8 is a temperature profile of a wooden wall.
Figure 9:
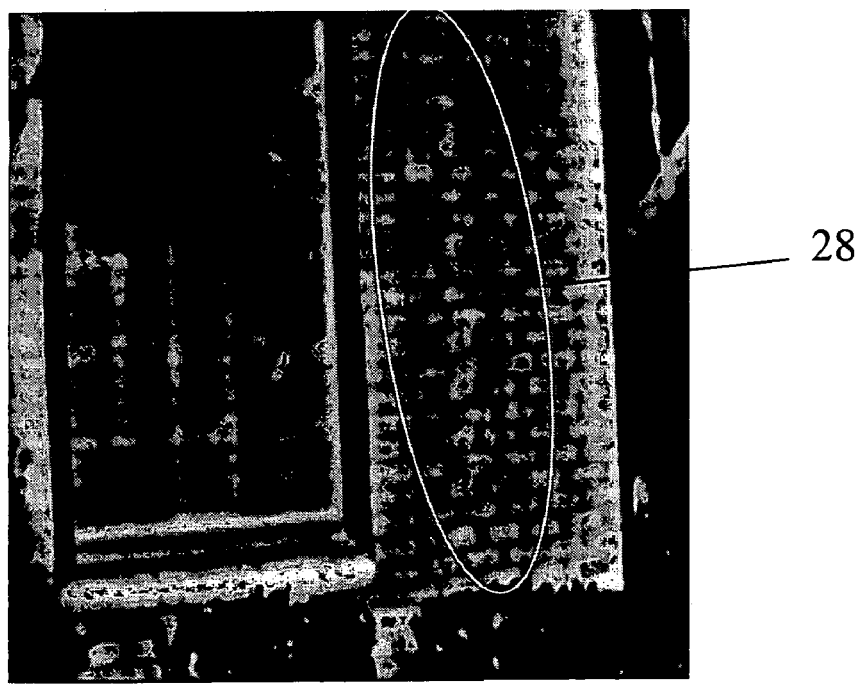
FIG. 9 is a temperature profile of a brick wall.

FIGS. 8 and 9 show temperature profile taken at noon. In FIG. 8, no thermal anomalies are present, while in FIG. 9, a thermal anomaly 28 shows a cracked brick wall. This temperature profile shows as a thermal anomaly because moisture is in the crack in the wall.

Figure 10A:
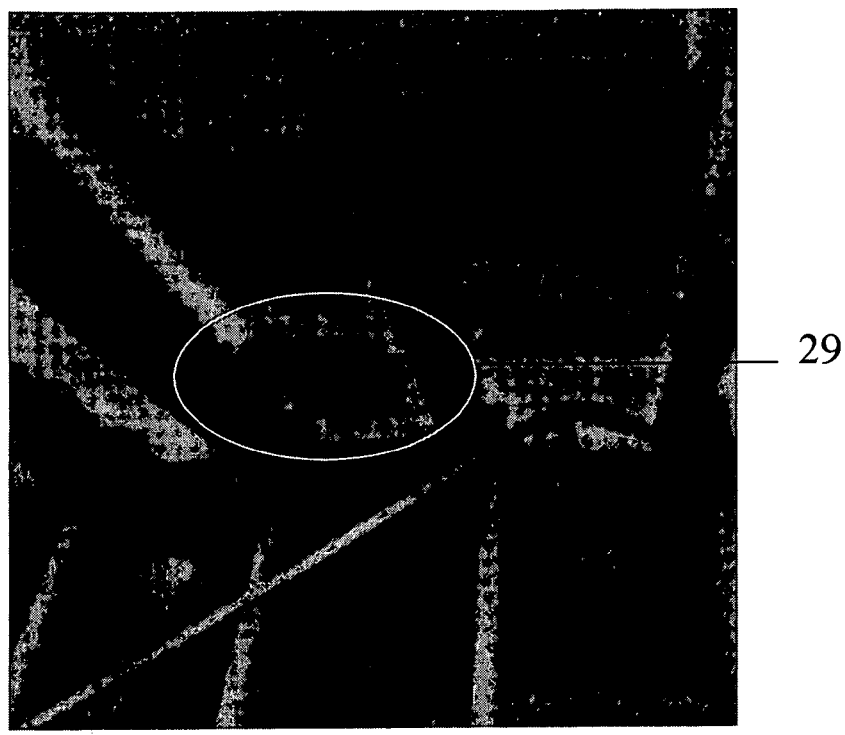
FIG. 10A is a temperature profile of the interior surface underside of a roof.
Figure 10B:
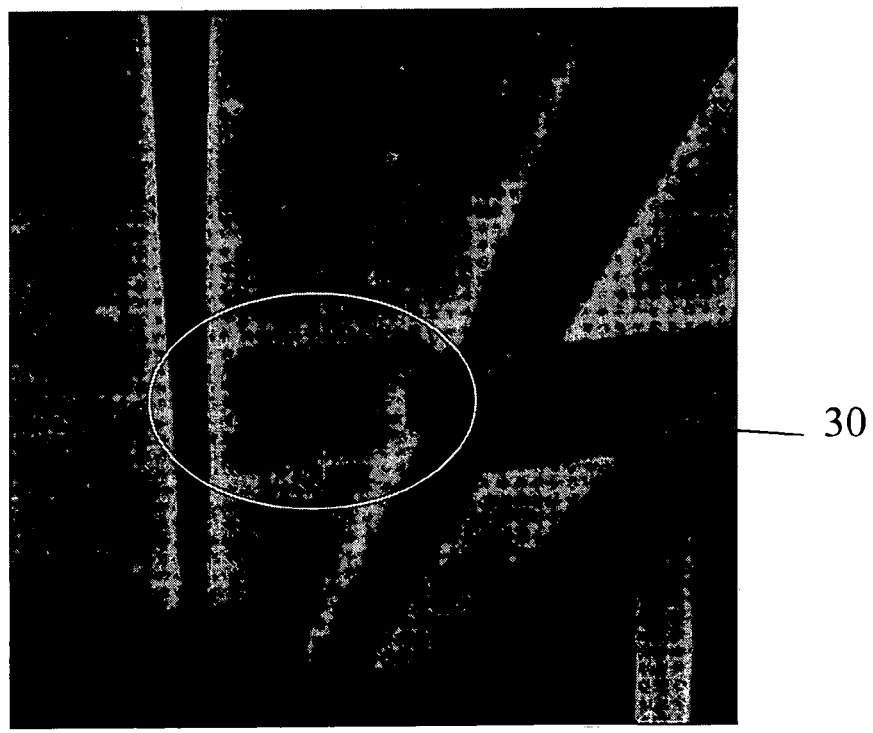
FIG. 10B is a temperature profile of the interior surface underside of a roof.

Roofs (Pitched Roof) Applications—In the heat of the day, the thermal load on a roof can be quite striking to view through an infrared detector. Anomalies show up as dark shadows against a bright background. More specifically, referring to FIGS. 10A and 10B, thermal anomalies 29 and 30 are shown as dark spots. This type of thermal anomaly is indicative of water damage to a roof. These types of thermal anomalies are present for two to three days after rain during the summer time and up to few weeks in the cold season. This period is considered the thermal window for this application. In the present method, a pitched roof is defined as a roof having a slope ranging greater than a rise of 1 by 12 inches.

A pitched roof is inspected by obtaining a temperature profile of the interior surface of the pitched roof from inside of the attic within three days of rain. This method using an infrared camera coupled to a digital camera can provide information on active water leaks prior to the leaks being visible. Water damage to a roof as seen from the interior of the attic space is revealed as dark shadows against the normally bright roof decking. When conducting this method, additional confirmation can be obtained by observing: (a) standing water below the stain or interior staining or water damage on finished surfaces; or (b) presence of moisture confirmed from results of moisture meter test; or (c) visible damage to the decking such as: presence of a dark stain coupled with positive moisture meter reading; or presence of visible active growths of mold or mildew; or decking delamination; or decking discoloration; or combinations of the above.

Figure 10C:
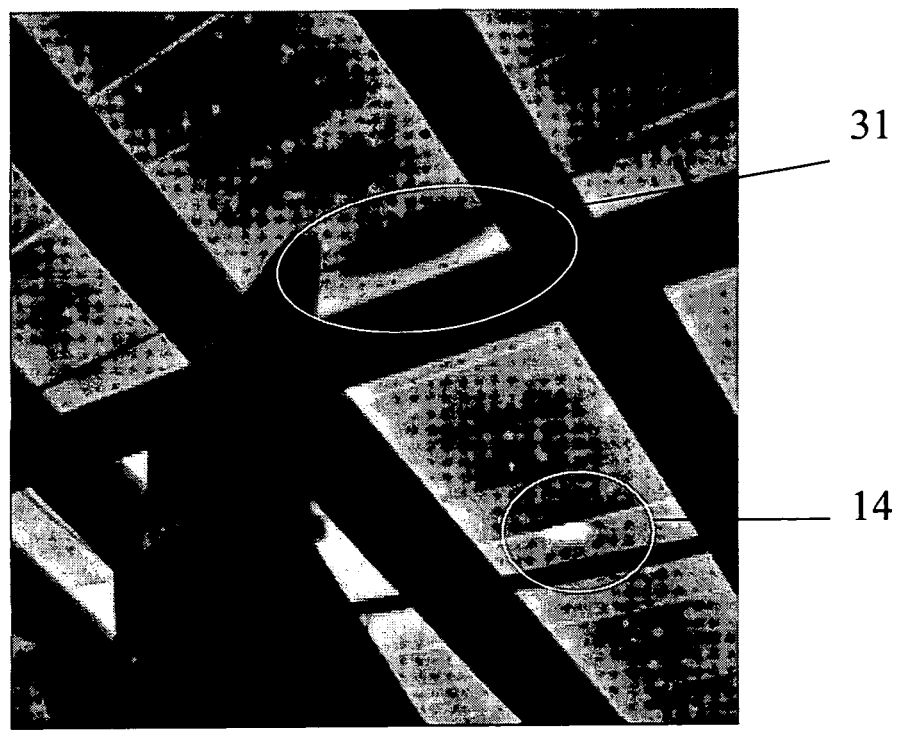
FIG. 10C is a temperature profile of the interior surface underside of a roof.

This invention can be applied to pitched roofs to inspect the condition of a residential roof. More specifically, in FIG. 10C the source of a leak can be traced by assessing the thermal anomaly 31. The leak can be followed from left to right to find the leak shown as the dark spot. Additionally, this method can also be used to detect structural deformation. The thermal anomaly shown as the white irregular spot 14 is indicative of a puncture in the roof decking material with the shingles covering over the puncture. This method can also be used to detect structural damage such as cracks. The temperature profile is recorded on a digital recording device 2.

Electrical Applications—Many problems in the electrical systems are the result of abnormal heating associated with high resistance or excessive current flow. Thermal imaging scan (Infrared thermography) allows us to see these invisible thermal patterns before damage occurs. A thermal imaging scan allows an inspector to quickly locate the suspicious electrical hot spots from among the hundreds and thousands of potential problems. The primary benefit of inspecting residential building electrical system is to increase safety.

When electricity (electrical current) flows through a circuit, part of the electrical current is converted into heat energy. This is due to the normal electrical resistance in the circuit. High resistance has been used to produce heat or light to make our life more comfortable. However, in many instances, heat is an unwanted by-product that results in energy lost, costly damage, and hazarded condition. For example, when resistance is unusually high due to an over fuse under size conductor, loose connection, rusted connection, defective switch, the circuit may become hot. Electrical components can become hot enough to melt the electrical insulation and result in a house fire.

There are two major categories of electrical hot spots: contact surface over heat and overload. 1. Contact surface over heat—This type of problem occurred when electrical current flow through a single point of contact with high resistance. They usually associated with rusted or warned out switch contact. The same problem can also occurred to electrical connector. 2. Overload—This type of problem occurred when high amount of current flow through a circuit. They usually associated with over fuse under size conductors.

Infrared detection provides another level of inspection for the electrical service throughout the house. This method to detect a potential overload of an electrical circuit in a residential building includes turning on substantially all light switches and exhaust blowers in a residential building. Next, a temperature profile is obtained of each electrical outlet in the residential building. The temperature profile is assessed for a thermal anomaly. If a thermal anomaly is detected, the next step can be to determine compliance with safety electrical guidelines.

Safety Electrical Guidelines: (1) make sure no over fuse (over breaker); (2) make sure proper grounding; (3) make sure no hot neutral reverse; (4) make sure no open ground; (5) Make sure all other electrical safety installation procedures are followed (such as aluminum wire, and GFCI.

The purpose of turning on substantially all of the light switches and substantially all of the exhaust blowers is to allow current to flow through the normal electrical loads while the inspector performs the exterior inspection. If a few light switches or blowers are missed, this still constitutes "substantially all". The order of which is turned on first is not important between the light switches and the exhaust blowers. During the time the inspector is inspecting the exterior portion of the house, the electrical system in the house has the opportunity to heat up under normal load. If an electrical circuit is drawing substantial amount of current that the circuit can't support, or in the case of faulty connections or faulty switches, the circuit will heat up and can provide a thermal signature indicating a potential problem with that particular circuit.

GFCI outlets and dimmer switch controls will always show a light heat signature in excess of surrounding materials because the GFCI outlet has an active circuit in operation at all times to test for electrical leakage. The dimmer switches are rheostats that adjust current flow to things like chandeliers, fans, etc. Since the current is adjustable, under maximum load the dimmer switch will also develop a heat signature in excess of that of the surrounding materials. Do not construe these normal heat signatures to mean that an inspector should not evaluate each dimmer switch or GFCI outlet. On the contrary, the inspector should take time to determine if the temperature differential is unusually high for each of the above. If the dimmer switch or switch plate cover is hot to the touch or 30 degrees F. higher than the surrounding wall temperature, further investigation is warranted. The same is true of a GFCI that is unusually warm or hot to the touch.

Figure 11:
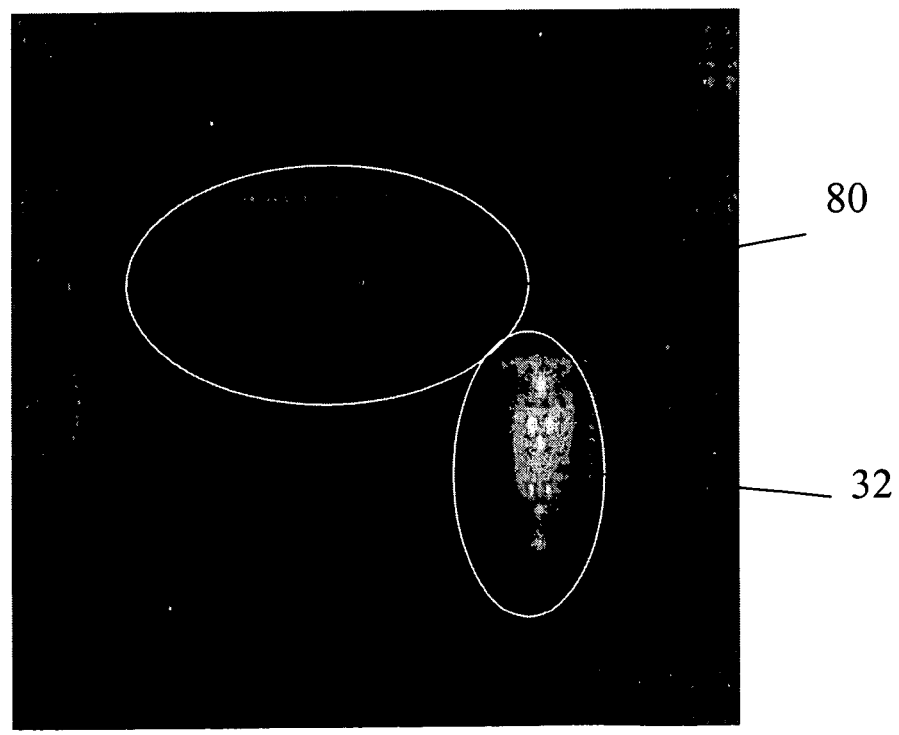
FIG. 11 is a temperature profile of electrical component.
Figure 12:
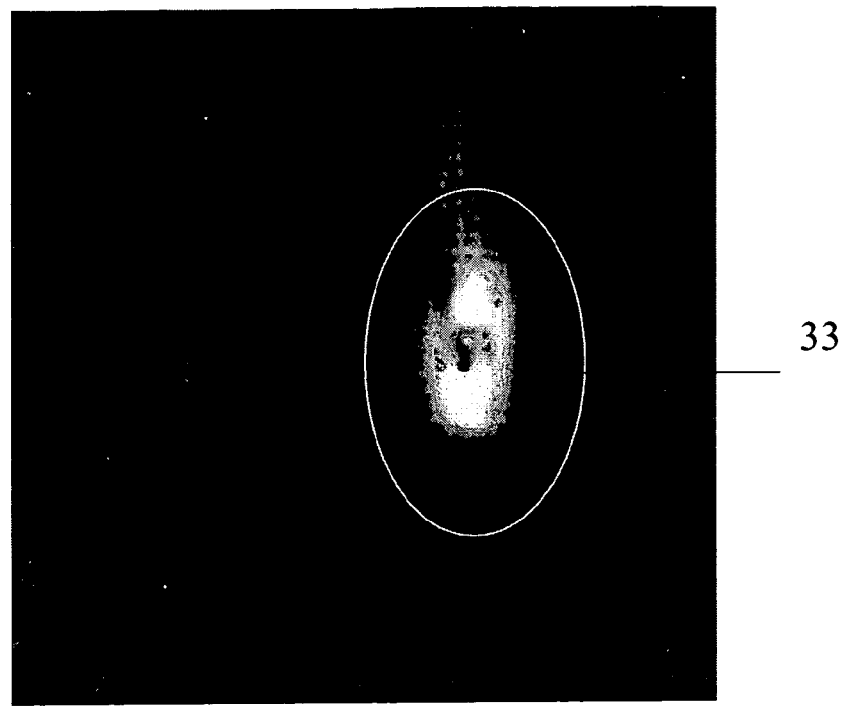
FIG. 12 is a temperature profile of an electrical component.
Figure 13A:
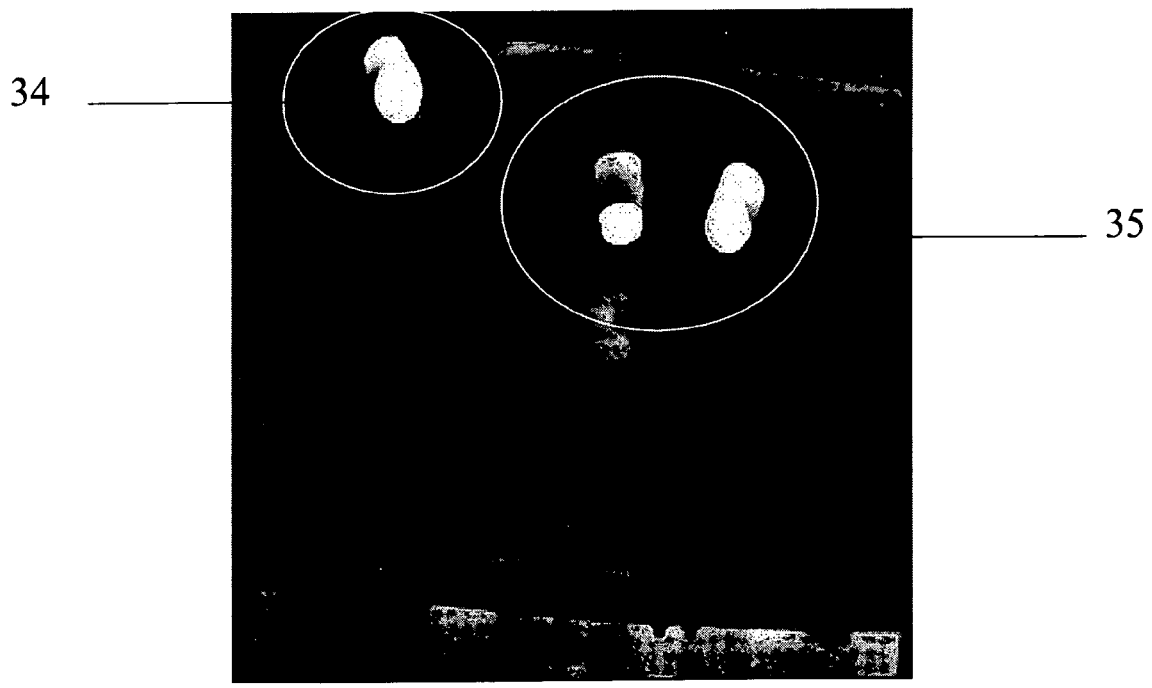
FIG. 13A is a temperature profile of an electrical component.
Figure 13B:
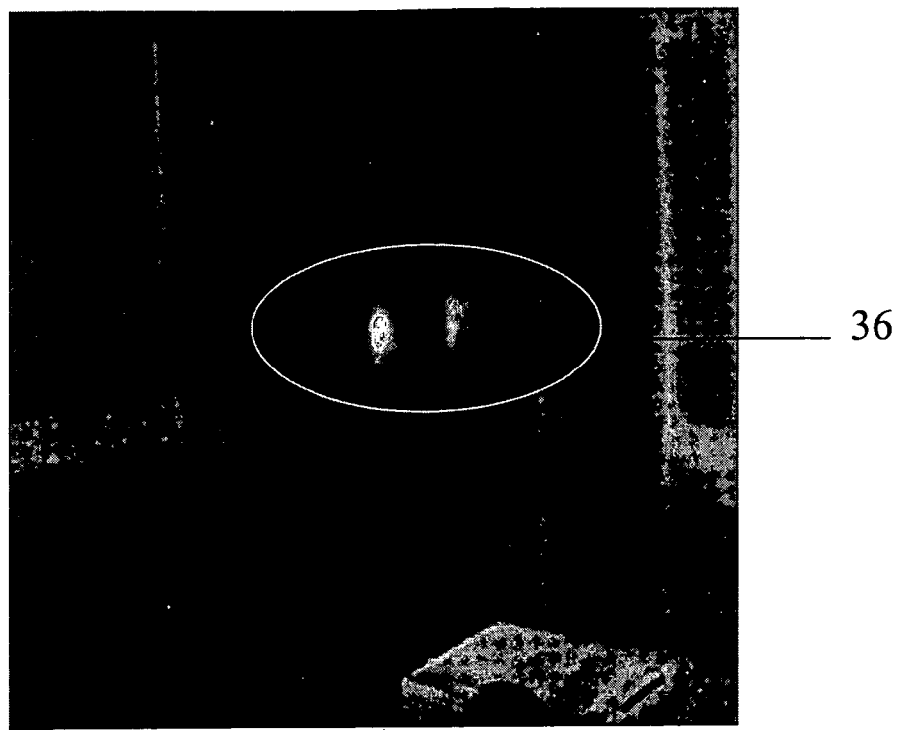
FIG. 13B is a temperature profile of an electrical component.
Figure 13C:
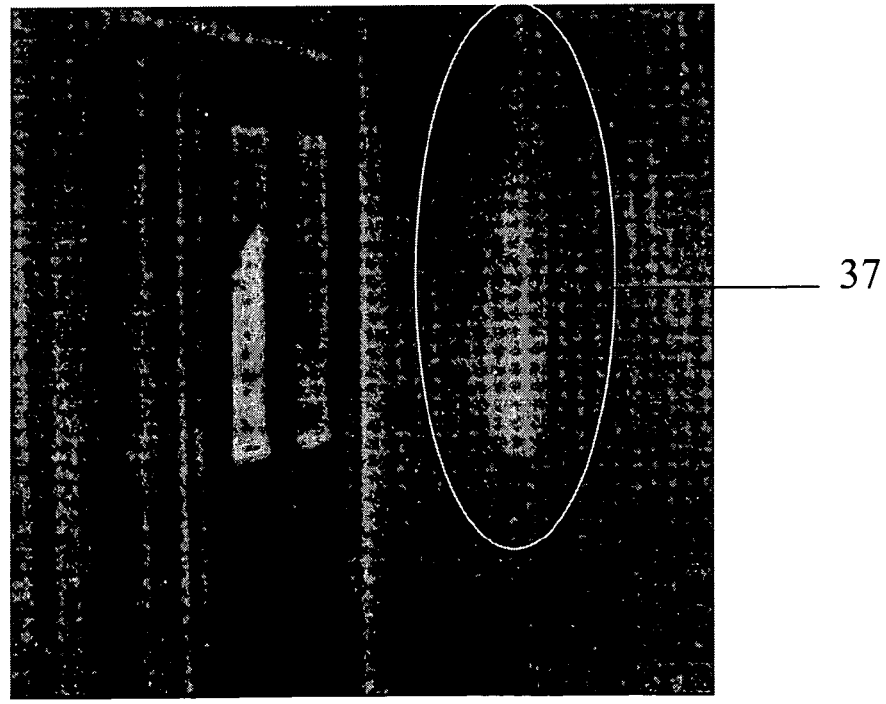
FIG. 13C is a temperature profile of an electrical component.
Figure 13D:
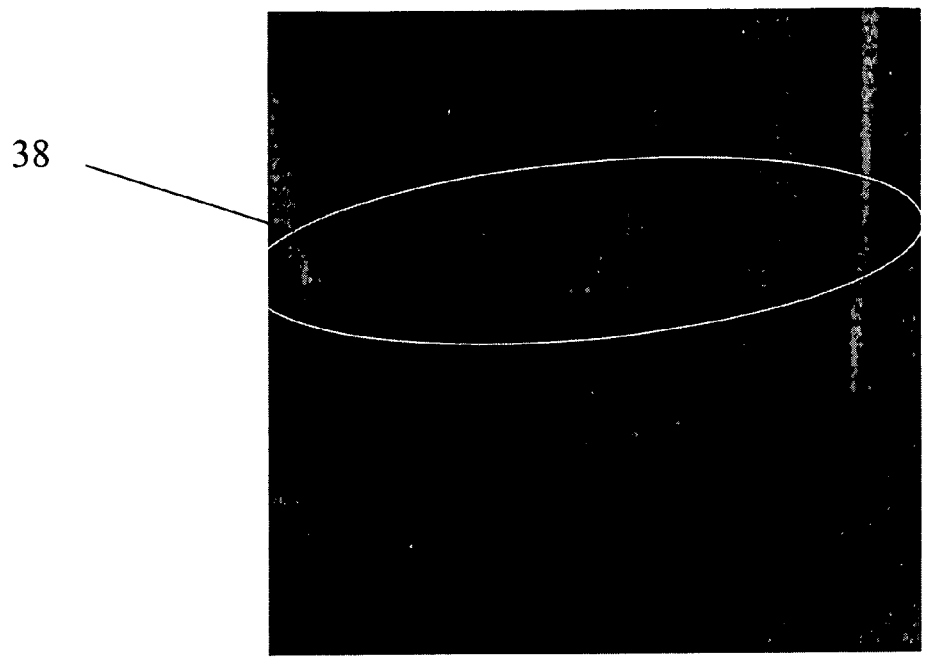
FIG. 13D is a temperature profile of an electrical component.
Figure 13E:
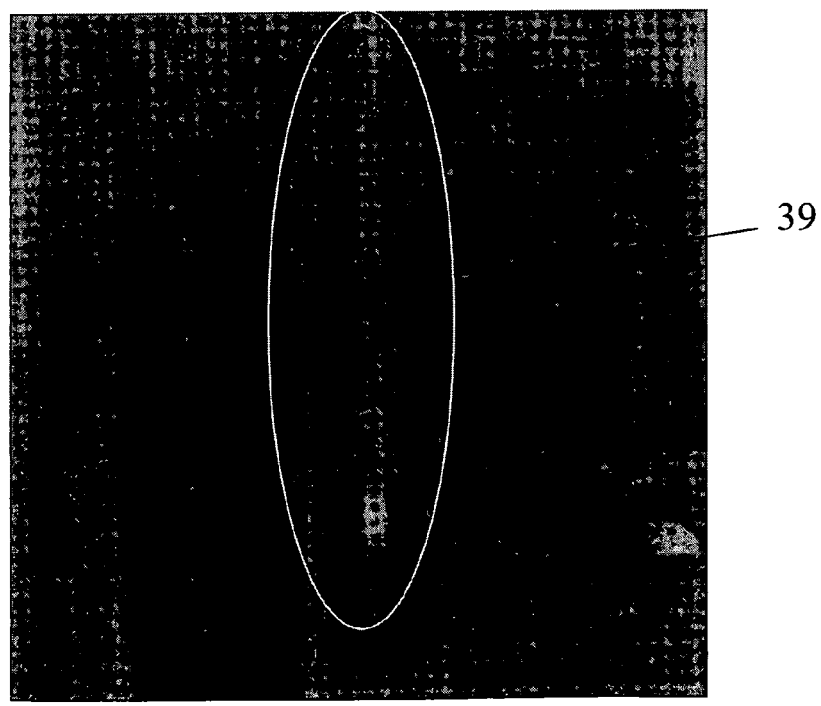
FIG. 13E is a temperature profile of an electrical component.

Referring to FIGS. 11, 12, 13A and 13B, various temperature profiles of electrical components are shown. These temperature profiles are made as part of a process to detect a potential problem with an electrical circuit of a residential building. In this method, the first step is to turn on substantially all of the light switches in the residential building. Then, a temperature profile, such as those shown in FIGS. 11, 12, 13A and 13B is obtained. Each of the temperature profiles is assessed for an anomaly. For example, FIG. 11, shows an on/off switch 80 and a GFCI outlet 32 that are normal. FIG. 12, is a temperature profile of a dimmer switcher that shows an anomaly 33 indicative of a very hot dimmer switch. Similarly, FIGS. 13A and 13B show thermal anomalies 34-36 indicative of heavily loaded electrical circuits. FIGS. 13C-E show a thermal anomaly indicative of a hot electrical wire 37-39. When a thermal anomaly is detected, the next step, in the preferred embodiment, is to direct the designated entity to consult with a licensed electrician.

Interior Residential Applications—The interior building components of a residence can be thermally scanned. The interior building component includes: wall insulation, plumbing, structural members and air ducts.

The inspector should turn on the heating/air conditioning by setting the interior thermostat(s) to 10° F. above or below the ambient exterior temperature shortly after arrival on site. When outdoor temperature is above 70° F., turn on the air conditioner to 10° F. lower. When outdoor temperature is less than 70° F., turn on the heat to 10° F. higher. This provides two of the three major requirements to obtain a suitable thermal gradient within a house: 1) increasing temperature differential between finished surfaces and interior ambient air temperature, and 2) interior air movement throughout the living spaces of the home. The temperature differential provides the gradient. The moving air enhances the gradient and sharpens the contrast between hidden moisture within structures and substrates and other areas within the structures or substrate, permitting the thermal camera to visually illustrate those thermal differences.

Figure 14A:
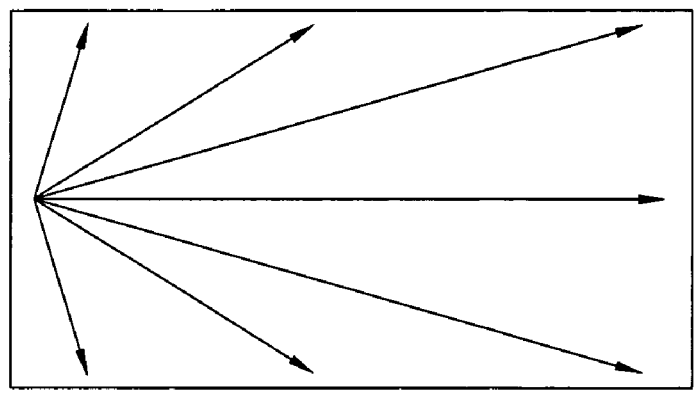
FIG. 14A is a schematic drawing of a method to scan.
Figure 14B:
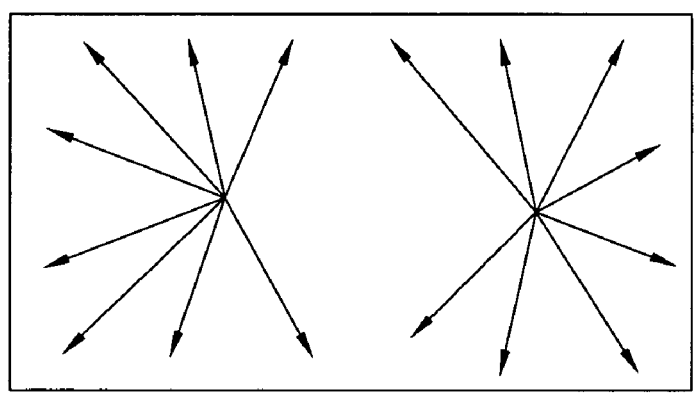
FIG. 14B is a schematic drawing of a method to scan.
Figure 14C:
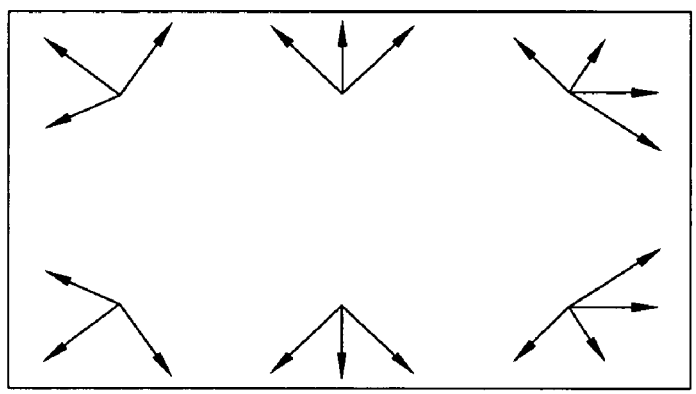
FIG. 14C is a schematic drawing of a method to scan.

Referring to FIGS. 14A, 14B and 14C, a method to scan an interior residential building component is disclosed. In the first step of this scanning method, an operator using the thermal imaging camera 1, digital recording device 2 and harness apparatus 3 shown in FIG. 1 scans from afar as shown in FIG. 14A. Next, the operator scans from mid-range pointing the imaging camera 1 from two equidistant points in a room as shown in FIG. 14B. In the next step, as shown in FIG. 14C, a scan from close range is accomplished by scanning a plurality of points within a smaller arc. Different inspectors may have a different way of scanning the interior of the building; however, any method adopted should be systematic to insure completeness. The combination of the use of the harness apparatus 3, the use of a systematic method to scan and the use of the methods to improve image contrast result in a rapid method to nondestructively inspect a residence.

When assessing the temperature profile, it is important for the inspector to confirm the dark spots are not due to: (1) improper setting of the infrared camera; (2) cold air from HVAC or cold outside air; (3) water pipes; (4) knots of wood; and (5) improper installation of insulation.

(1) Insulation—Infrared wall inspection can some time be confusing due to various reasons. The following discussion provides a basis to review thermal scans conducted in different seasons.

Figure 15:
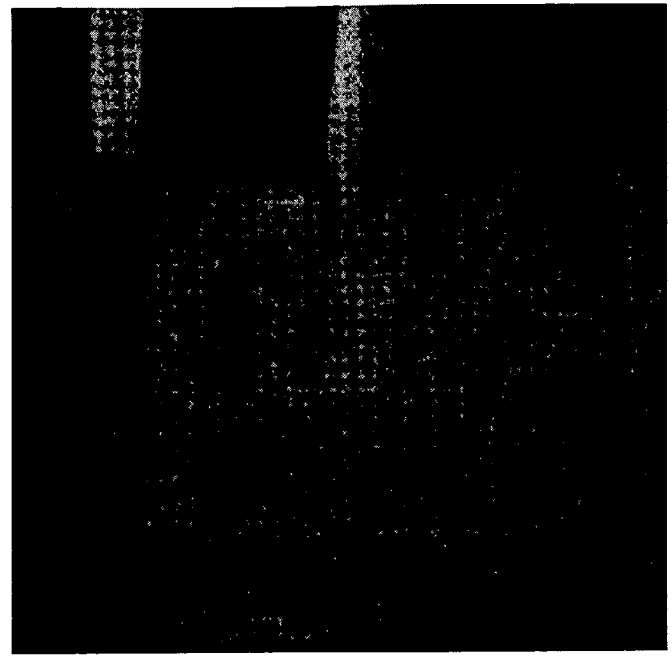
FIG. 15 is a temperature profile of a residential interior component.

Now referring to FIG. 15, 2×4 studs and ceiling rafters appear as cold in a well-insulated wall during the winter season. This is due to the fact that insulation is a relatively poor heat conductor as compared to 2×4 wood stud ceiling rafters, as a result, 2×4 wood stud ceiling rafters lose relatively more heat than the insulation (from indoor to outdoor).

Figure 16:
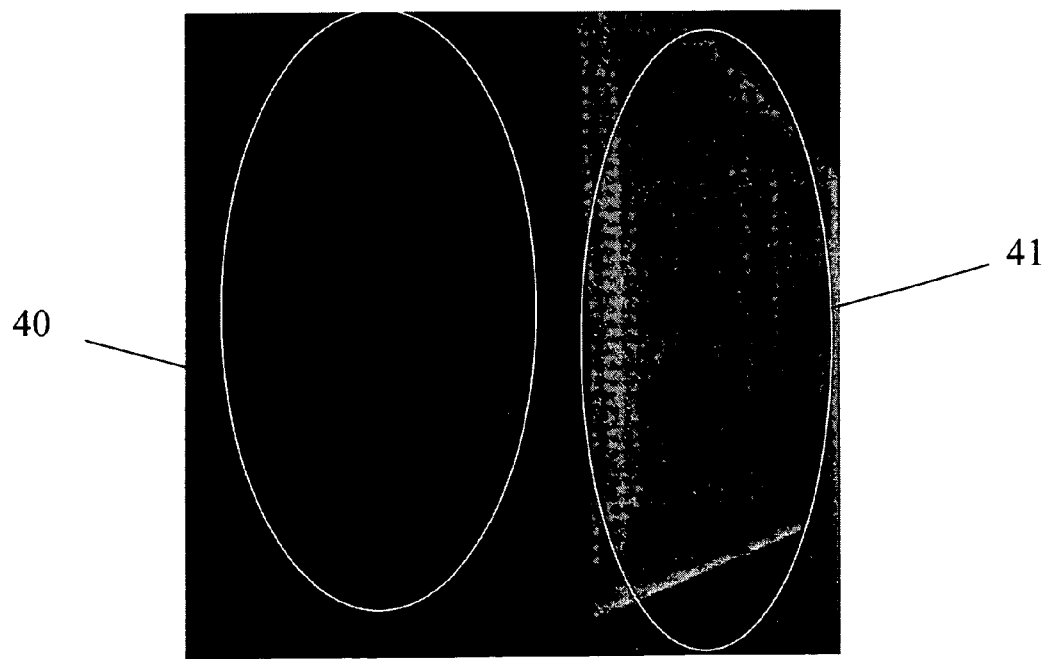
FIG. 16 is a temperature profile of a residential interior component.
Figure 17:
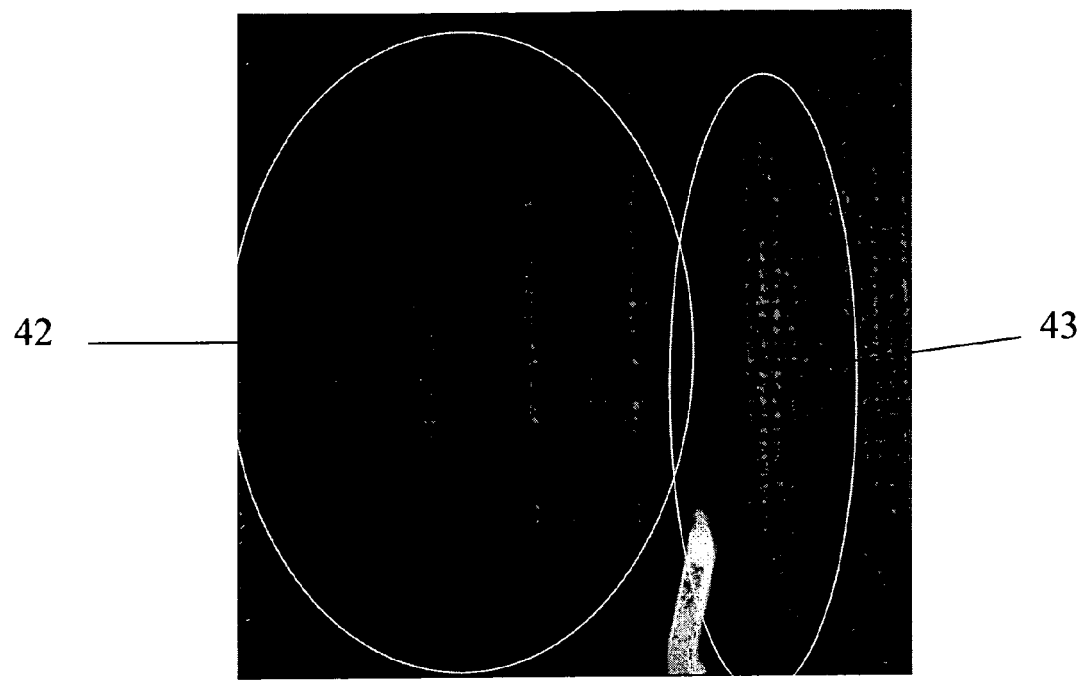
FIG. 17 is a temperature profile of a residential interior component.

Now referring to FIGS. 16 and 17, 2×4 studs 40 and 42 appear as warm in uninsulated or very poorly insulated wall (left half of the wall) during the winter season. This is due to the fact that 2×4 wood stud now is a relatively better insulator as compared to uninsulated air space, as a result, the 2×4 stud looses relatively less heat than the uninsulated air space (from the indoor to the outdoor). The right portion 41 and 43 appears to be insulated.

Figure 18:
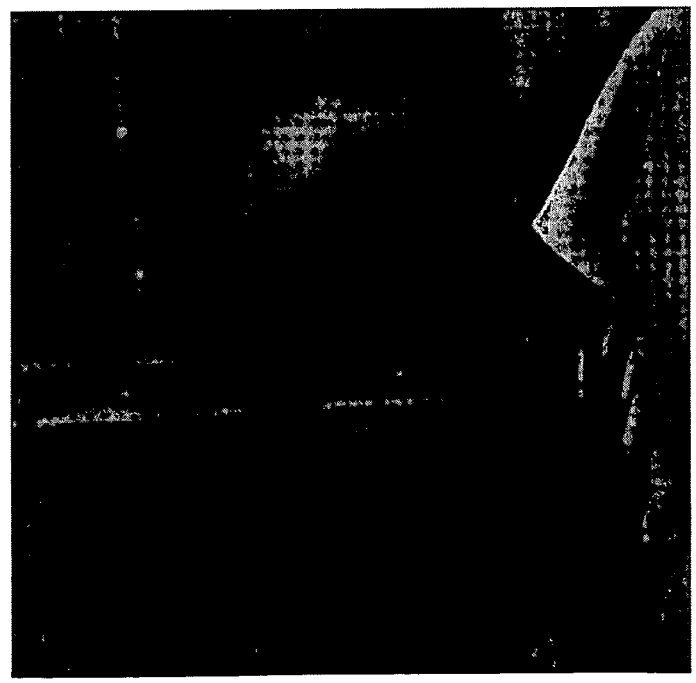
FIG. 18 is a temperature profile of a residential interior component.

Now referring to FIG. 18, 2×4 studs appear as warm in a well-insulated wall during the summer season. This is due to the fact that 2×4 wood stud is a relatively good heat conductor as compare to insulation between studs; as a result 2×4 studs conducts more out door heat then the insulated wall section.

Figure 19:
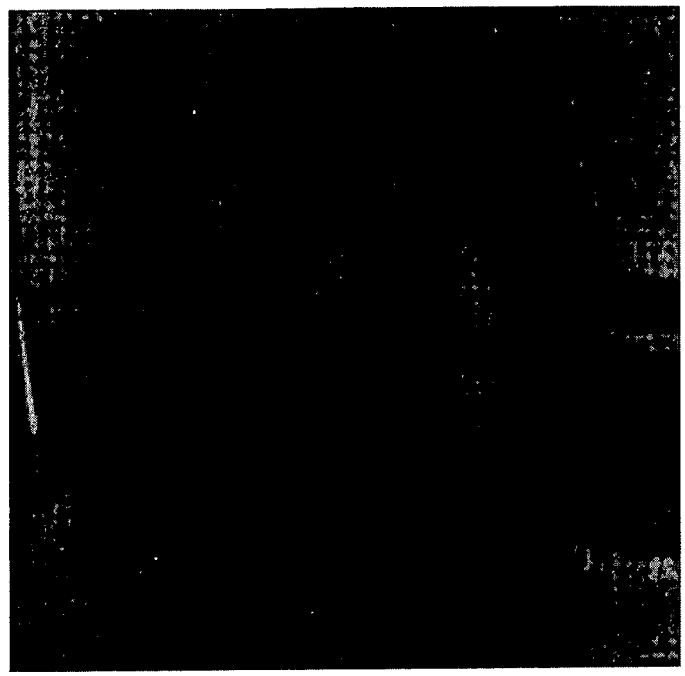
FIG. 19 is a temperature profile of a residential interior component.

Now referring to FIG. 19, 2×4 studs appear as cold in uninsulated or very poorly insulated wall during the summer season. This is due to the fact that the 2×4 wood studs now is a relatively better insulator as compare to uninsulated or poorly insulated air space, as a result 2×4 now conducts relatively less outdoor heat than the uninsulated or very poorly insulated wall section. The wall and ceiling of a residential building can be inspected to determine if they are uninsulated using this method. FIGS. 16, 17 and 19, show temperature profiles indicative of uninsulated interior building components.

Figure 20A:
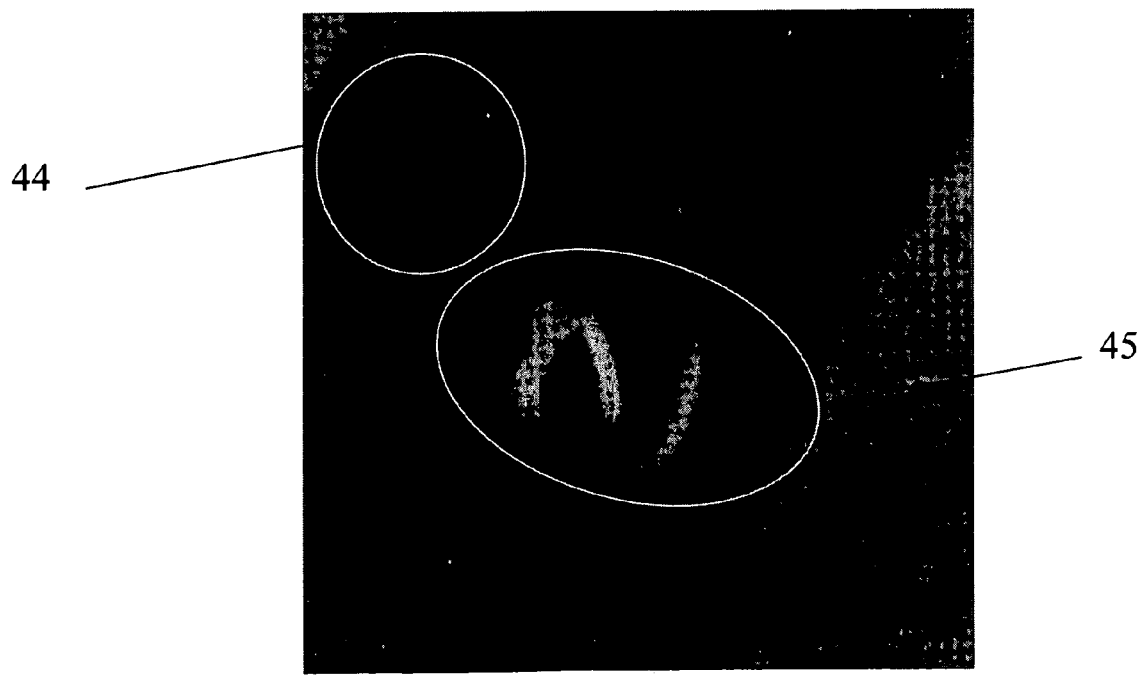
FIG. 20A is a temperature profile of a residential interior component.
Figure 20B:
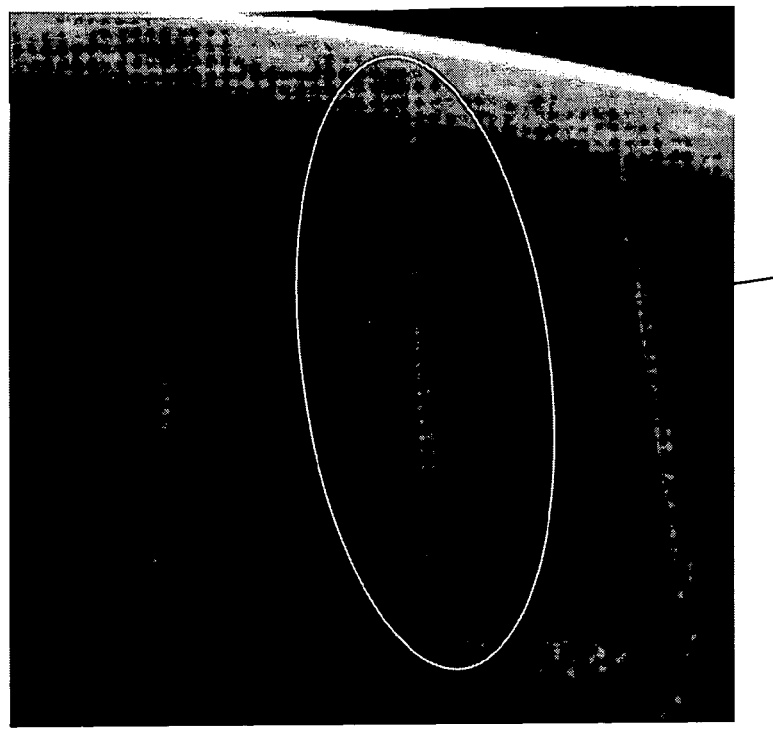
FIG. 20B is a temperature profile of an air conditioning duct.

(2) Plumbing—Hidden plumbing leaks can pinpoint within finished surfaces utilizing the thermal camera in cases where visual inspection was not possible. In FIG. 20A, a temperature profile is obtained for plumbing fixtures after the thermal window is created. The term plumbing fixture can include the plumbing fixture itself or associated piping. The temperature profile is recorded on a digital recording device and reviewed for a thermal anomaly. The temperature profile shown in FIG. 20A shows anomalies 44 and 45, which are indicative of a moisture leak behind the wall. FIG. 20B shows an air conditioning Freon pipes with a darker portion 46 indicative of low pressure (cold) return pipe. The temperature profile of FIG. 20B is a normal profile for an air conditioning duct.

(3) Condensation—Poorly managed moisture in a building can cause considerable damage that is often concealed for some time. Moisture in vapor form in the air causes no harm to building. However, when this moisture condenses to liquid form at the wrong place, damage can occur. The tricky part is, this often happens in areas that are difficult or impossible to see (within wall cavity) or difficult to determine the cause behind the problem. In the event of water leakage in a building, as the water begins to evaporate it produces a colder area, which can also be easily registered by the infrared sensor (camera).

In the wintertime the air in an average house at 70° F. and 40% relative humidity will be saturated and will condense to water droplets when the temperature drops to 45° F. It is not too difficult to understand how indoor air leaking into a wall or attic space will cool quickly. The outside of your walls and underside of the roof in your attic space is much closer to the outdoor temperature. When this bundle of warm moist indoor air leaks out through the wall or ceiling, it will cool and condense in the wall or ceiling/roof.

Figure 21A:
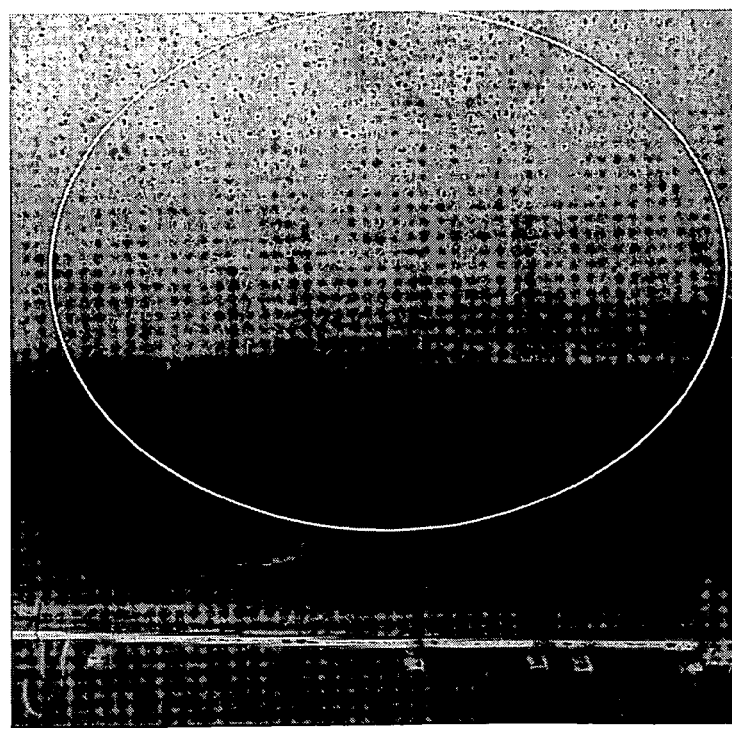
FIG. 21A is a temperature profile of a residential interior component.
Figure 21B:
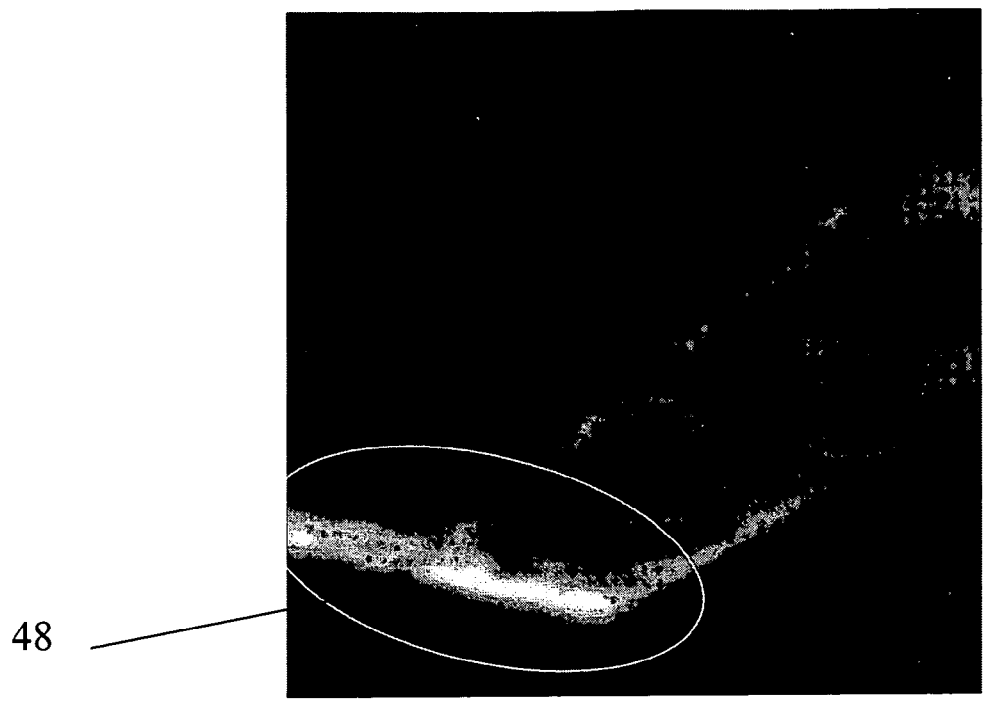
FIG. 21B is a temperature profile of a residential interior component.

Condensation can also occur on interior ceiling surface as shown in FIGS. 21A and 21B. FIG. 21A was taken 4 feet away from the ceiling. The anomaly 47 is indicative of moisture on the ceiling. The temperature profile shown in FIG. 21B was taken 15 feet away from the same ceiling shown in FIG. 21A. The anomaly 48 is indicative of moisture in the ceiling.

Figure 21C:
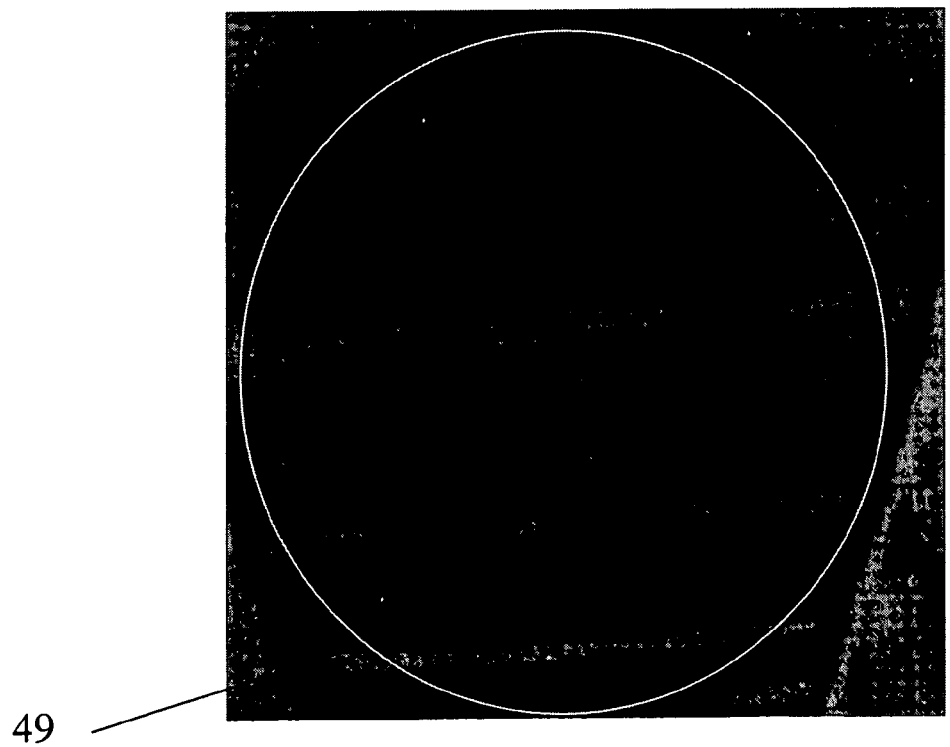
FIG. 21C is a temperature profile of a residential interior component.
Figure 21D:
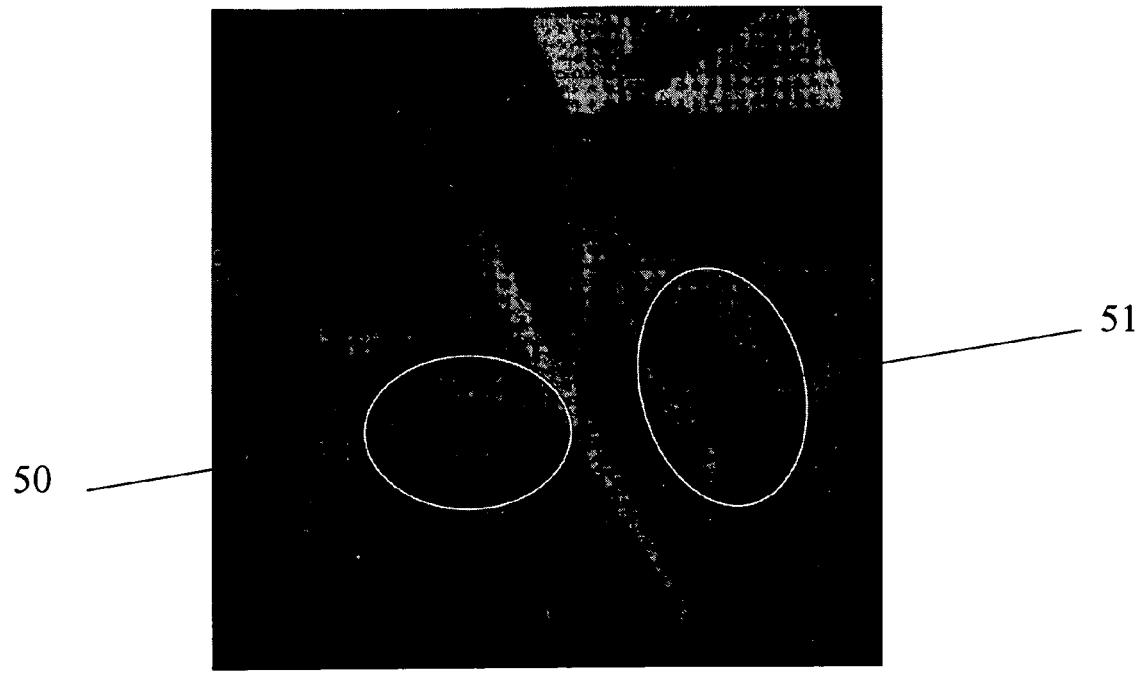
FIG. 21D is a temperature profile of a residential interior component.

(4) Moisture in Air Duct—Additionally, FIGS. 21C and 21D show anomalies 49-51 which are indicative of moisture in an air duct. This happens most often when there is no insulation in that particular section of the ceiling due to poor workmanship or due to rodent activities plus the occupant of the house has the lifestyle of generating high level of moisture with inadequate ventilation during the winter season. The uninsulated ceiling is closer to the cold outdoor temperature. When the high level moisture indoor air comes in contact with the cold interior ceiling surface (the hotter the air, the higher it rises and more moisture it can hold), it will cook and condense. These types of condensation problems were often mistaken as roof leaks. This happens when there is insufficient insulation around the air duct and poor workmanship or aging insulation. Condensation accumulates in cold air (in summer) eventually dripping into the ceiling under the duct.

(5) Mold—Condensation in building can cause mold. Building materials that remain wet for between 24 to 48 hours have the potential for mold developing and developing quickly. Molds thrive on organic material and eventually eat away at the material. Cellulose material such as ceiling tile, dry wall, insulation, books, carpeting, upholstered furniture, curtains, food and etc. Remediation of mold: The most important thing is to find the source of causing the mold to grow, which is the moisture. A good mold investigator focuses on locating moisture not microbiology or sampling. Condensation, construction techniques, and water intrusion lie at the heart of a proper mold investigation. Mold issues begin and end with moisture issues—Caoimhin P. Connell (Senior Industrial Hygienist for Colorado industrial hygiene and oxicological consulting firm). The method for inspection of interior residential components can be applied to locate the source of moisture. The source of the moisture can be correlated with mold growth.

There is a limit to how much moisture can be stored. Wood is able to safely store up to 20% moisture by weight. Moisture levels above this can cause rot, mold and mildew. The preset method can be used to locate moisture and correlate this moisture with mold growth.

Figure 22:
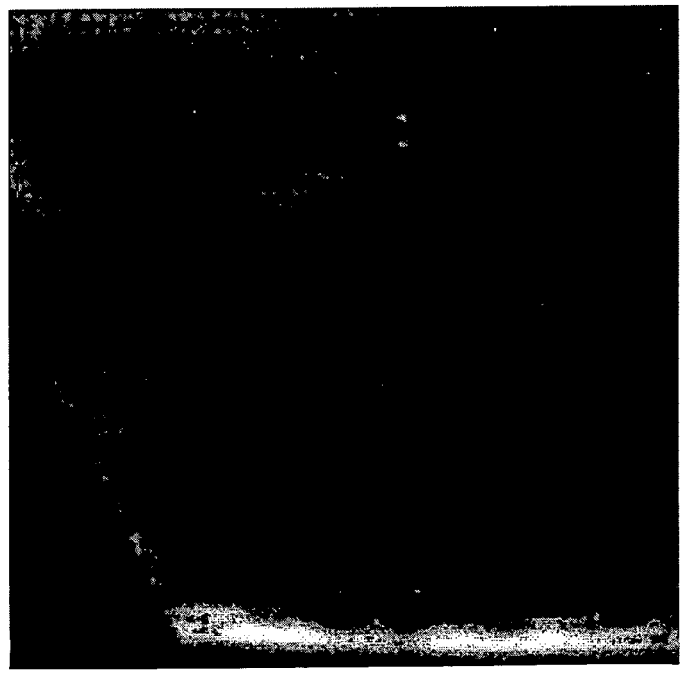
FIG. 22 is a temperature profile of a residential interior component.
Figure 23:
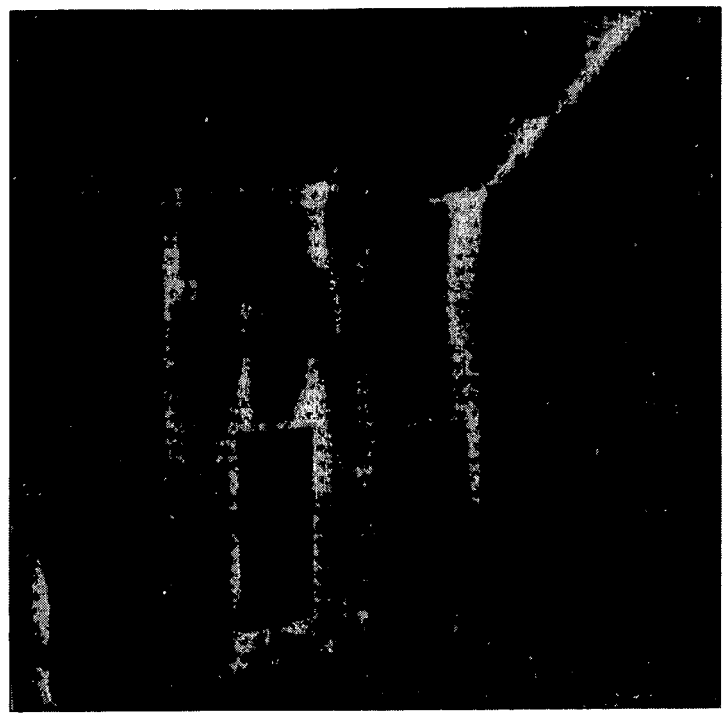
FIG. 23 is a temperature profile of a residential interior component.

(6) Small Animals—As for small animals, such as mice, rats, squirrels, and etc. when they infest a house attic or wall space, they tend to burrow through insulation, creating air gaps in the normally evenly distributed insulation and thereby changing the thermal properties of the insulation, leaving visual evidence of tunnels and nests that would normally be invisible to even the trained eye. FIGS. 22 and 23 are thermal profiles of an interior component of a residential building. A review of a digital recording of this thermal profile shows an anomaly that is interpreted as tunnels in insulation in the ceiling (FIG. 22) a tunnel in the insulation in the walls (FIG. 23).

Figure 24:
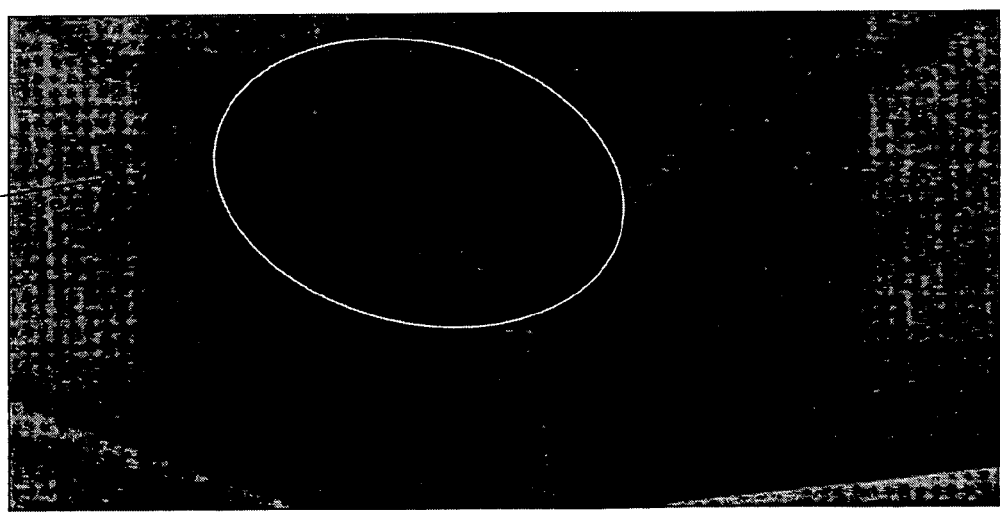
FIG. 24 is a temperature profile of a residential interior component.
Figure 25:
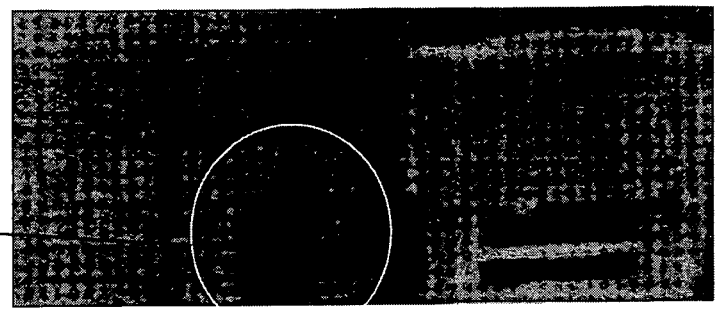
FIG. 25 is a temperature profile of a residential interior component.

(7) Structural Misalignment or Damage—In the case of less than perfect construction techniques, the trained observer can spot missing, mis-aligned or damaged internal structural members such as studs, headers, trimmers and the like. In some cases, those damaged or missing members may contribute to otherwise unaccounted for interior damage that would normally point to foundation troubles, but which are, in fact, framing problems. FIGS. 24 and 25 are temperature profiles of wall internal components of a residential building. In FIG. 24, the thermal anomaly 52 is indicative of a structural misalignment. In FIG. 25, the thermal anomaly 53 is indicative of a structural misalignment. A review of the digital recording of the thermal profile shows an anomaly this is indicative of structure misalignment.

Figure 26:
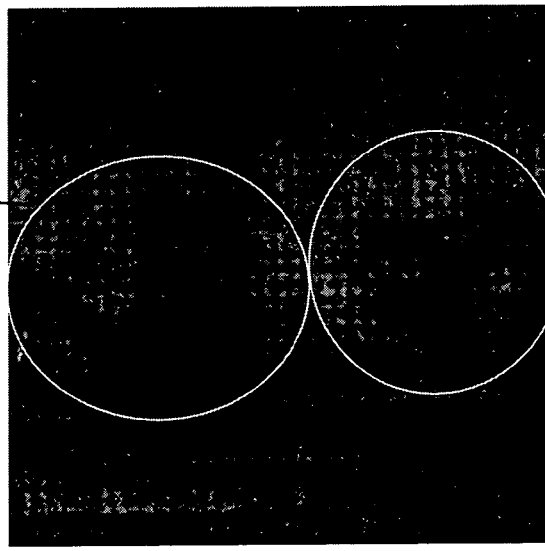
FIG. 26 is a temperature profile of a residential interior component.
Figure 27:
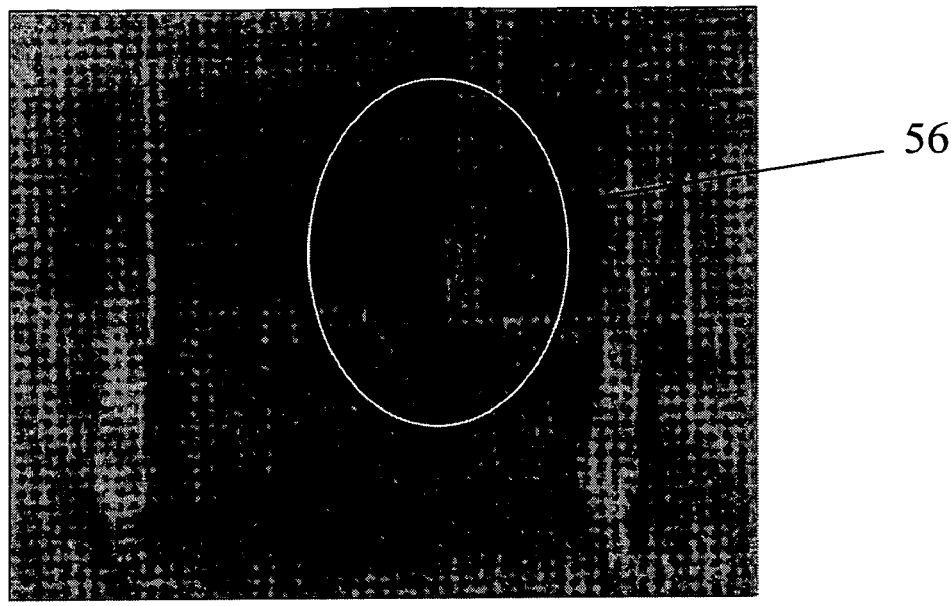
FIG. 27 is a temperature profile of a residential interior component.

(8) Wood Destroying Insect—Pests such as termites and even mouse and rat infestations have been recorded because of the telltale thermal discrepancies their respective environments provide. In the case of native termite species, these destructive pests require moisture in order to survive at high humidity levels. The thermal imaging system provides an additional tool for discovering the presence of termites and increases the detection of an active colony from about 30% (traditional inspection method) to at least 60%. This means that while the sensor system cannot detect 100% of all termite infestations, it can measurably double the chances of finding active colonies that have not been discovered through traditional inspection. FIGS. 26 and 27 are thermal profiles indicative of suspected termite infestation. More specifically, FIG. 26 shows to thermal anomalies and 54 and 55 indicative of suspicious wood destroying insect infestation. Similarly, FIG. 27 shows an anomaly 56 indicative of wood destroying insect infestation. The presence of wood destroying insects can be confirmed by an acoustic scan. The protocol for an acoustic scan is set out in U.S. Ser. No. 10/680,377 filed Oct. 7, 2003.

Figure 28:
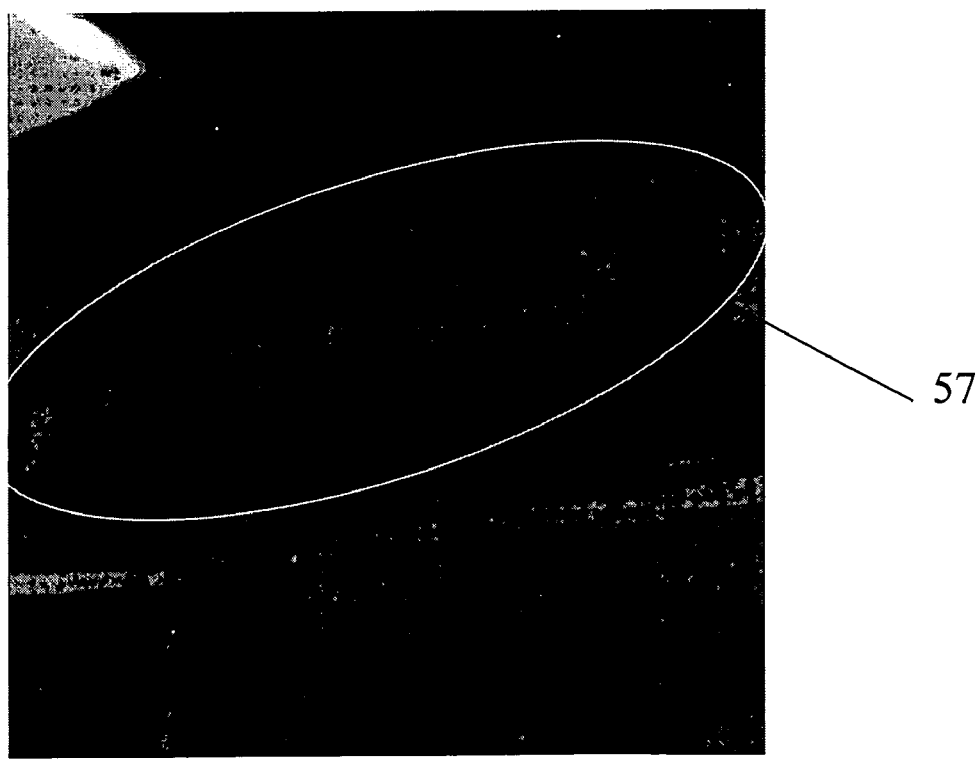
FIG. 28 is a temperature profile of a residential interior component.
Figure 29:
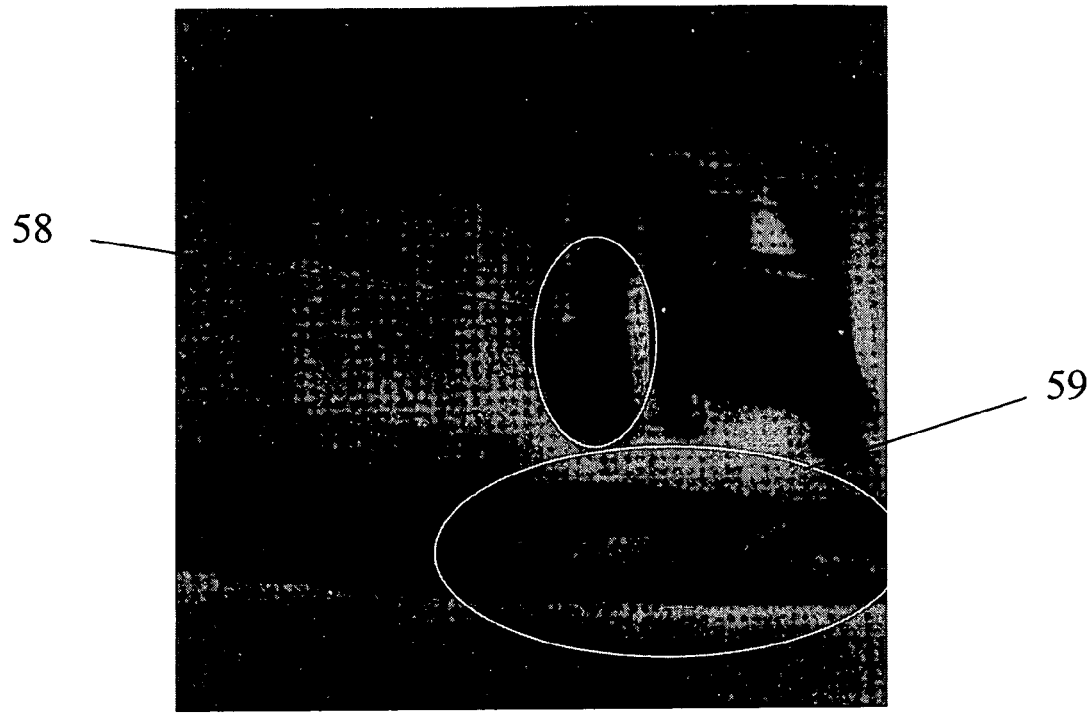
FIG. 29 is a temperature profile of a residential interior component.

(9) Air Duct Leakage—FIGS. 28 and 29 show a temperature profile indicative of air duct leakage. In these temperature profiles, the anomalies 57-59 are indicative of air leaking out of an air duct. The black is cold air leakage in the summer (in the winter it would be opposite).

(10) Inspection of basement wall (water leaks through cracks, pipes, etc.)—The application of the present thermal imaging techniques provides the ability to distinguish areas of relative temperature difference. This means that cool areas appear dark relative to warmer areas, which appear lighter. Relative temperature can be seen under these conditions. The first is different thermal characteristics of the building components, the second is actual differences in temperature, and the third is the ability of heat to be removed from the substrate by evaporation. The mere presence of moisture within or exterior to a building component does not guarantee that the thermal camera will show that moisture is present. There has to be a way for evaporation to permit heat loss. Without the ability to evaporate, water will take on the temperature of the substrate, and the equipment will be blind to the presence of the moisture. It should be recalled in order for the camera to distinguish relative differences in temperature, there has to exist a temperature difference of 0.08° C. or greater between residential building components.

Thus, to inspect a basement, if it is necessary, to create air flow to the basement area by: (a) Open heating or cooling air outlet if they are closed (wait for at least 30 Minutes before infrared scan); (b) Open all basement doors or windows (wait for at least 30 minutes before Infrared scan); and (c) Create artificial air flow by using portable force air heater (wait for at least 30 minutes before infrared scan).

Figure 30:
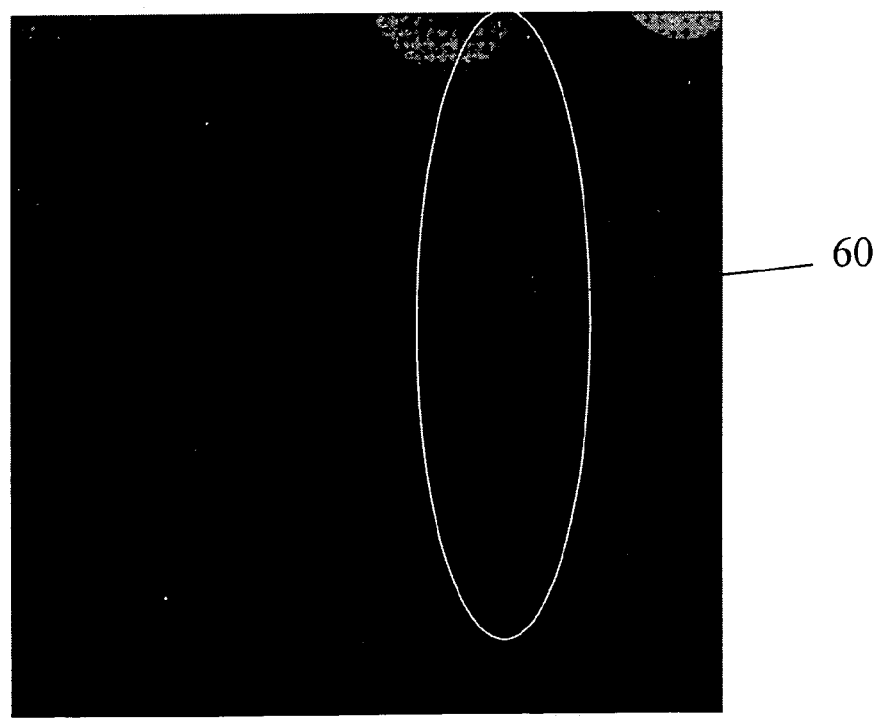
FIG. 30 is a temperature profile of a residential interior component.
Figure 31:
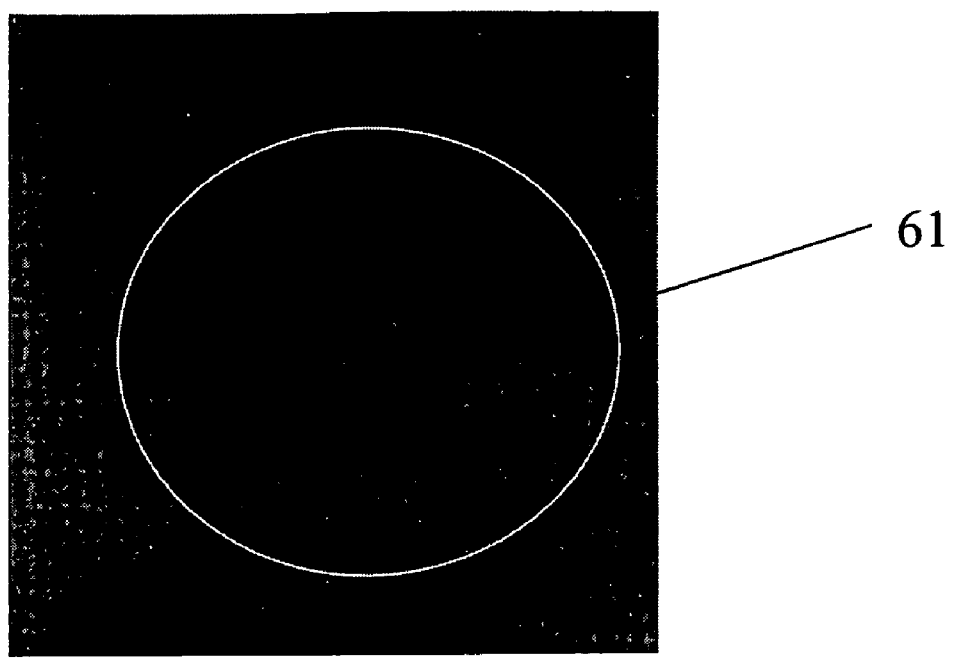
FIG. 31 is a temperature profile of a residential interior component.

FIGS. 30 and 31 are temperature profiles indicative of moisture penetrating through cracks in a basement wall. More specifically, in FIGS. 30 and 31, anomalies and 61 and 70 are indicative of moisture on a basement wall.

The temperature profiles database library is made of a compilation of numerous temperature profiles in different settings, areas and conditions over a period of years. In this regard, the system may be used as an experimental set-up to capture recordings of temperature profiles that can be used as reference patterns for comparison with future captured temperature profile patterns. The temperature profiles database library can also be used as a valuable training tool for training future inspectors. This invention also provides a method for facilitating a computerized method for inspection of a residential building. This method involves maintaining a database of temperature profiles for residential building components at a computerized, centralized facility. The temperature profiles can be input to the computer via a wireless transmission means such as wireless internet connection or by a non-wireless transmission means, such as a disk, a cable and infrared transmission.

An application database management program, such as SAP or Oracle, can be used to set up fields, such as, type of anomaly, normal residential building component, residential building component with an anomaly, and a specific designated residential building. The fields are used to facilitate scanning the database for a selected temperature profile. Thus, if one is interested in, for example, a specific residential building, all temperature profiles relating to a specific house are selected. For example, a specific residential structure can be inspected on a periodic basis, and the temperature profiles can be maintained in a field in the database. These inspections can occur on different days such as three times a year. A printer driver on the hard drive of the computer is used to control a printing device to print a report showing selected temperature profiles of residential building components.

Although the present invention has been described and illustrated with respect to preferred embodiments and a preferred use thereof, it is not to be so limited since modifications and changes can be made therein which are within the full scope of the invention.

The invention claimed is:

1. A method to rapidly inspect residential building components for a designated entity comprising the steps of:
preparing a residential building for inspection by creating a temperature differential of greater than 10° F. between, the inside and the outside of said residential building and turning on substantially all light switches and substantially all exhaust blowers in said residential building; and then
obtaining temperature profiles of the exterior residential building components selected from the group consisting of wall, cafe and facia wherein said temperature profiles detect moisture;
obtaining temperature profiles of the interior surface of a pitched roof wherein said temperature profiles detect moisture;
obtaining temperature profiles of the interior residential building components;
obtaining temperature profiles of each electrical outlet in the residential building;
assessing each of said temperature profiles to detect a thermal anomaly indicative of a problem with said residential building components wherein said problem can include moisture; and
reporting said problem to said designated entity wherein said steps up to the step of assessing each of said profiles occur within 4 hours.

2. A method to detect a potential electrical problem in a residential building comprising the steps of:
preparing said residential building to detect a potential electrical problem by turning on substantially all light switches in said residential building; and turning on substantially all exhaust blowers in said residential building; and then
obtaining temperature profiles of substantially all electrical outlets in said residential building; and assessing each of said temperature profiles for an anomaly indicative of an electrical problem, wherein said steps up to the step of assessing each of said profiles occurs within 4 hours.

3. The method of claim 2 wherein said electrical problem is an overload of an electrical circuit.

4. The method of claim 2 wherein said electrical problem is contact surface over heat.

5. The method of claim 2 wherein said electrical problem is hot electrical wire within a wall.

6. The method of claim 2 wherein said temperature profiles are recorded on a digital recording device.

7. The method of claim 2 further comprising the step of measuring the temperature of substantially all electrical outlets.

* * * * *

UNITED STATES PATENT AND TRADEMARK OFFICE
CERTIFICATE OF CORRECTION

PATENT NO.        : 7,445,377 B2                                Page 1 of 1
APPLICATION NO.   : 10/708571
DATED             : November 4, 2008
INVENTOR(S)       : Peng Lee and Kevin J. Seddon It is certified that error appears in the above-identified patent and that said Letters Patent is hereby corrected as shown below:

Column 16, line 17, the word in claim 1 reading "cafe" should be --eave--

Signed and Sealed this

Fourth Day of May, 2010

David J. Kappos
*Director of the United States Patent and Trademark Office*